United States Patent
Ahn et al.

(10) Patent No.: US 11,407,834 B2
(45) Date of Patent: Aug. 9, 2022

(54) ANTI-PD-L1 ANTIBODY AND USE THEREOF

(71) Applicant: PHARMABCINE INC., Daejeon (KR)

(72) Inventors: Sungho Ahn, Chungcheongbuk-do (KR); Miju Park, Gyeonggi-do (KR); Eun Hee Lee, Chungcheongnam-do (KR); Shin Ae Yi, Gyeonggi-do (KR); Sang Soon Byun, Daejeon (KR); Hyuk Joon Lee, Sejong (KR); Do-Yun Kim, Chungcheongbuk-do (KR); Jinsang Yoo, Daejeon (KR); Keunhee Oh, Chungcheongbuk-do (KR); Weon Sup Lee, Daejeon (KR); Jin-San Yoo, Daejeon (KR)

(73) Assignee: PHARMABCINE INC., Daejeon (KR)

( * ) Notice: Subject to any disclaimer, the term of this patent is extended or adjusted under 35 U.S.C. 154(b) by 110 days.

(21) Appl. No.: 16/957,903

(22) PCT Filed: Dec. 27, 2018

(86) PCT No.: PCT/KR2018/016715
§ 371 (c)(1),
(2) Date: Jun. 25, 2020

(87) PCT Pub. No.: WO2019/132533
PCT Pub. Date: Jul. 4, 2019

(65) Prior Publication Data
US 2021/0054078 A1    Feb. 25, 2021

(30) Foreign Application Priority Data
Dec. 27, 2017 (KR) .................. 10-2017-0180440

(51) Int. Cl.
*C07K 16/28* (2006.01)
*A61K 39/395* (2006.01)

(52) U.S. Cl.
CPC .... *C07K 16/2827* (2013.01); *C07K 2317/565* (2013.01)

(58) Field of Classification Search
None
See application file for complete search history.

(56) References Cited

FOREIGN PATENT DOCUMENTS

| KR | 20170023102 A | 3/2017 |
| KR | 20170039706 A | 4/2017 |
| KR | 20170102167 A | 9/2017 |
| WO | 2010089411 A2 | 8/2010 |
| WO | 2014055891 A1 | 4/2014 |
| WO | 2017215590 A1 | 12/2017 |

OTHER PUBLICATIONS

Rudikoff et al. 1982, Proc. Natl. Acad. Sci. USA, 79: 1979-1983.*
Panka et al., 1988, Proc. Natl. Acad. Sci. USA, 85: 3080-3084.*
Grenga, I. et al., "A Fully Human IgGI Anti-PD-LI MAb in an In Vitro Assay Enhances Antigen-specific T-cell Responses", Clinical & Translational Immunology, vol. 5, e83, 2016, 1-12.
EESR dated Oct. 6, 2021 for EP No. 18897350.7.

* cited by examiner

Primary Examiner — Ilia I Ouspenski
(74) Attorney, Agent, or Firm — Elmore Patent Law Group, P.C.; Joseph C. Zucchero; Carolyn S. Elmore

(57) ABSTRACT

Disclosed are an anti-PD-L1 antibody or an antigen-binding fragment thereof, a nucleic acid encoding the same, a vector including the nucleic acid, a cell transformed with the vector, a method for producing the antibody or an antigen-binding fragment thereof, a pharmaceutical composition for preventing or treating cancer containing the same, and a composition for co-administration with an antibody other than an antibody binding to PD-L1, containing the same.

9 Claims, 9 Drawing Sheets

Specification includes a Sequence Listing.

[Figure 1]
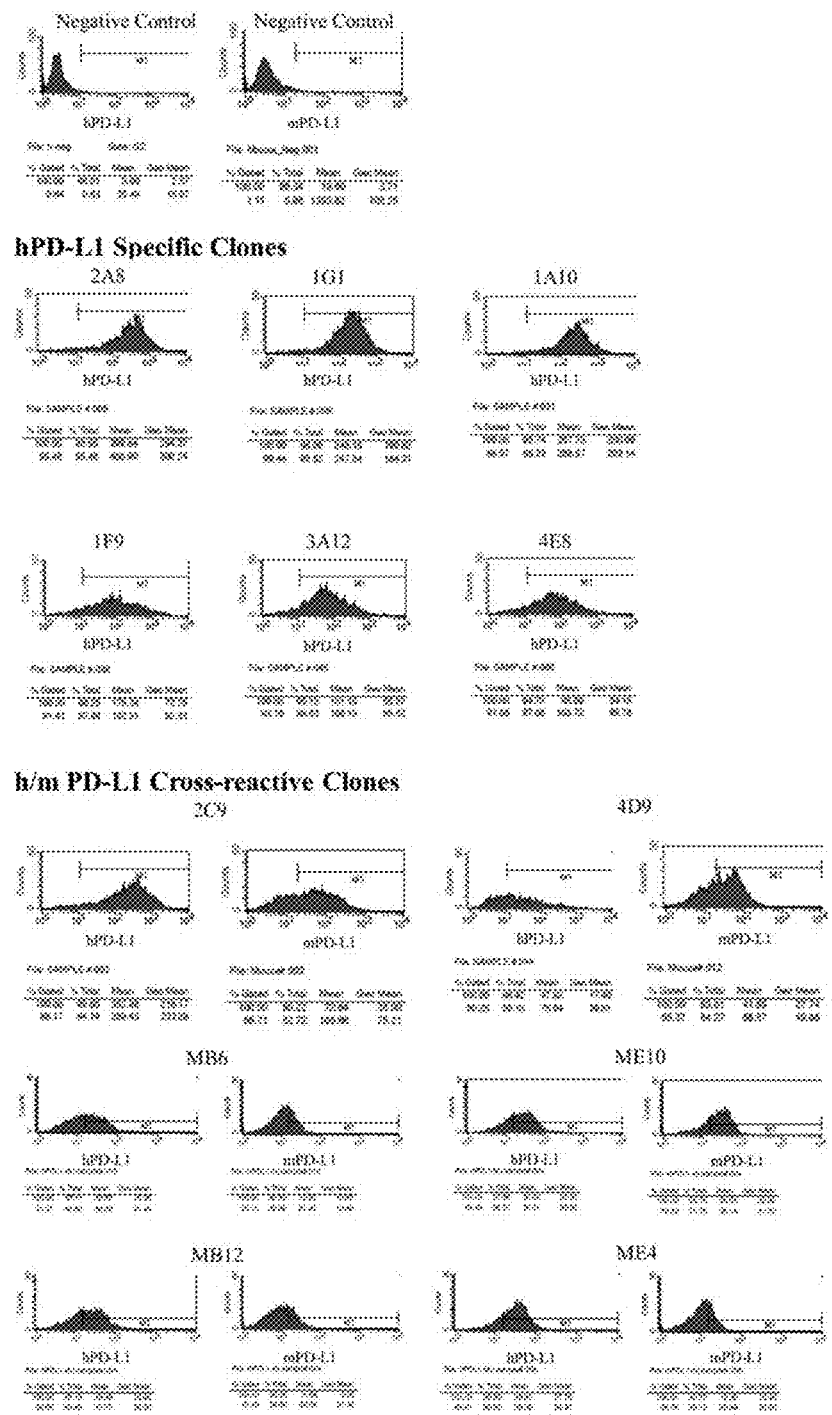

[Figure 2]
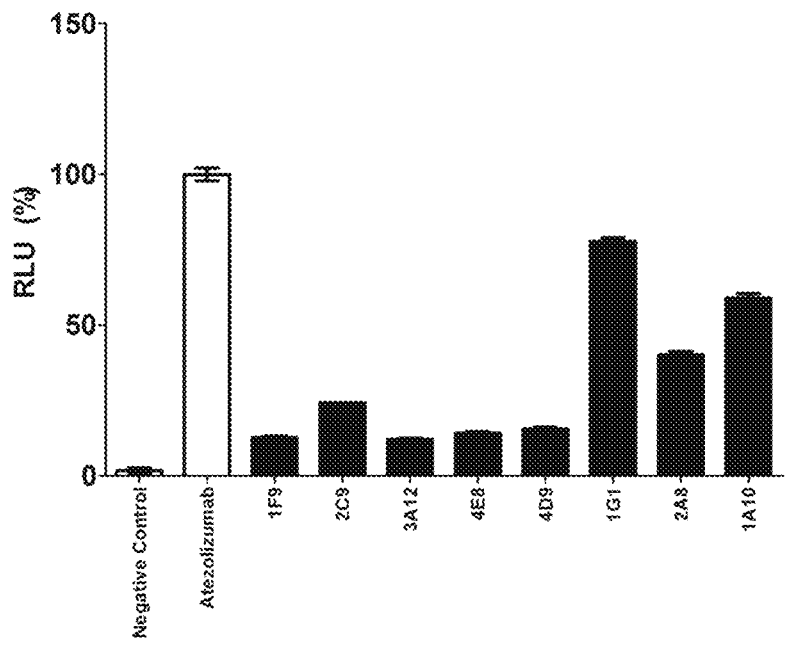
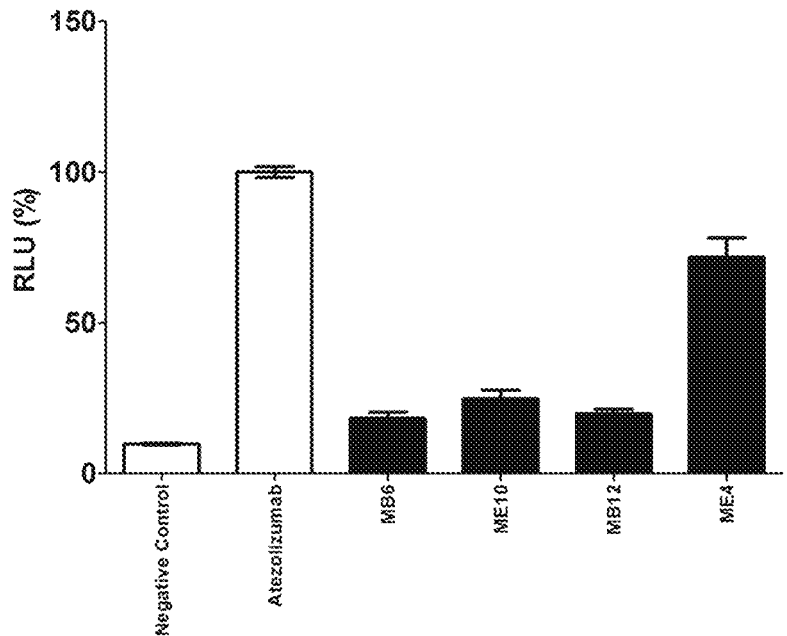

[Figure 3]
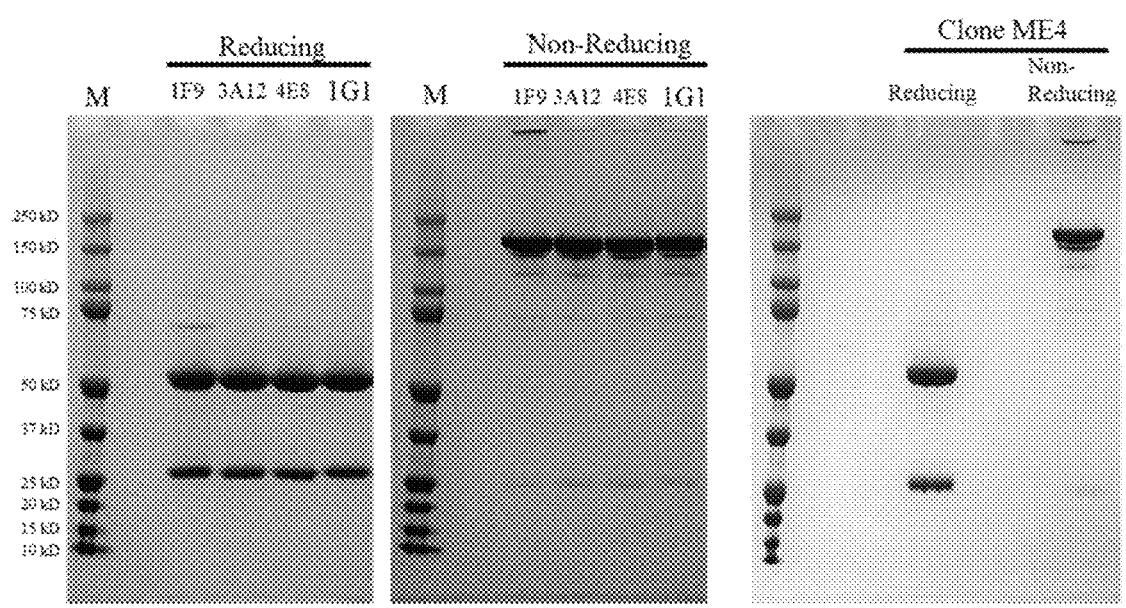

[Figure 4]
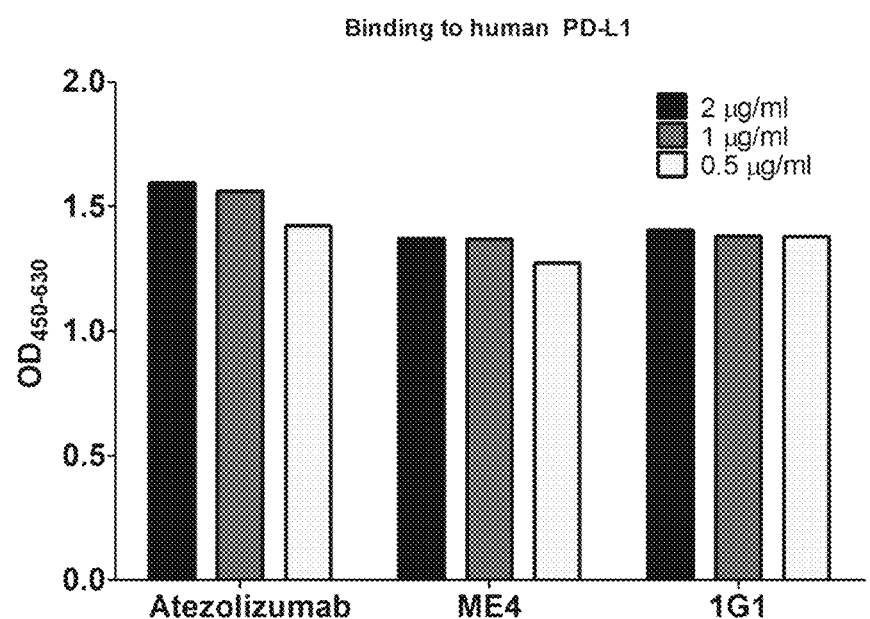
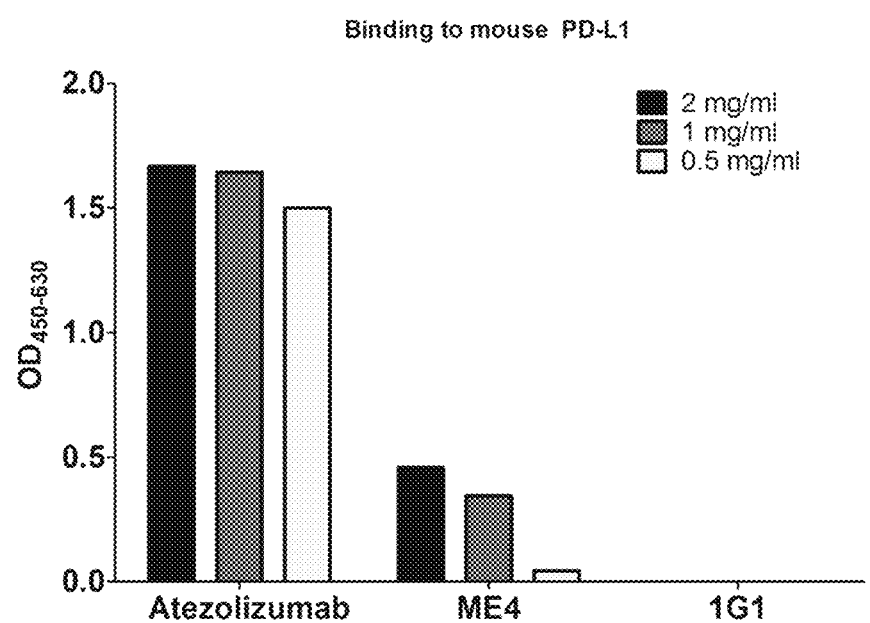

[Figure 5]
hPD-L1/CHO-K1
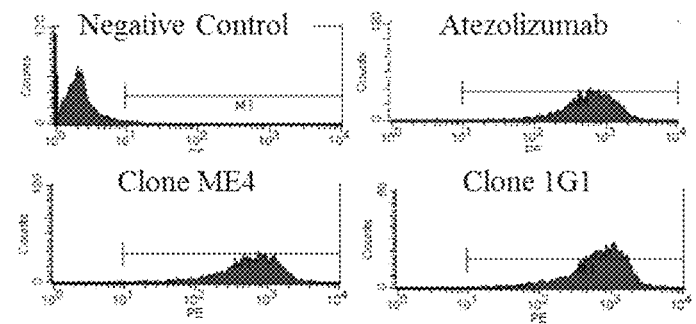
mPD-L1/CHO-K1
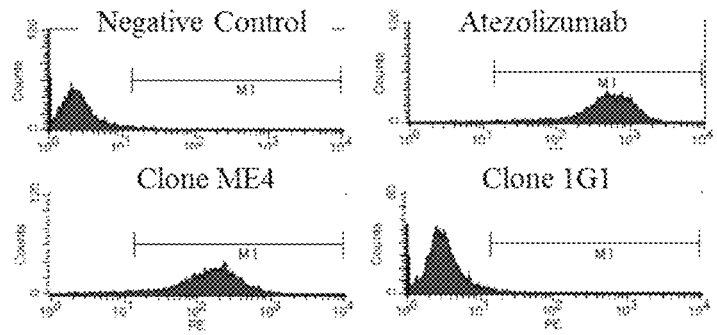

[Figure 6]
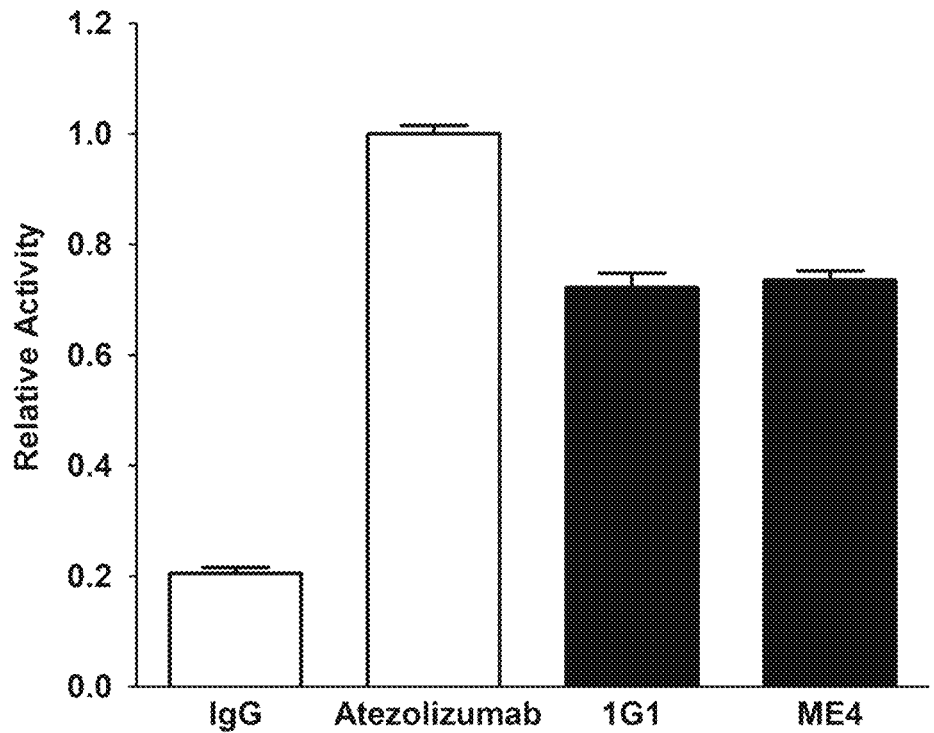
[Figure 7]
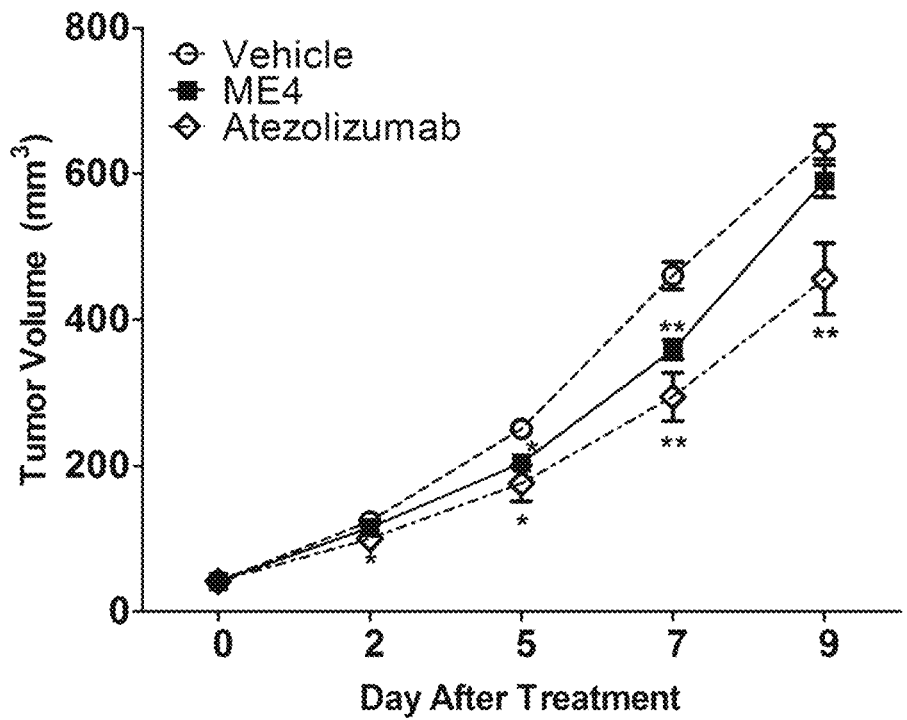

[Figure 8]
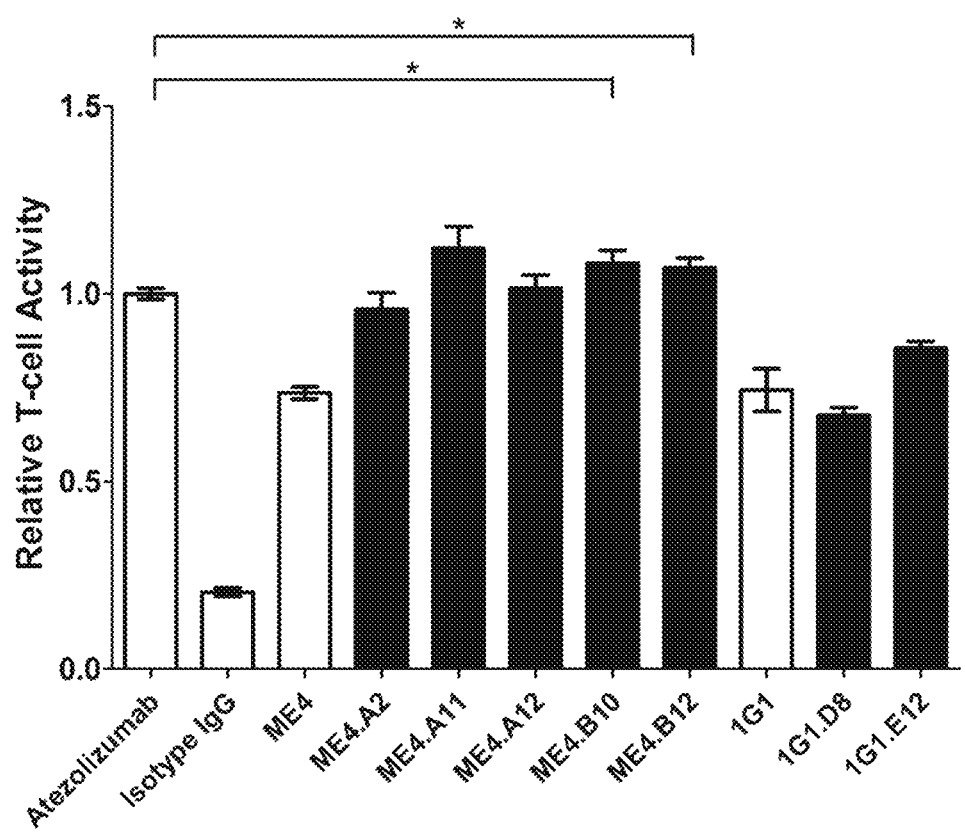

[Figure 9]
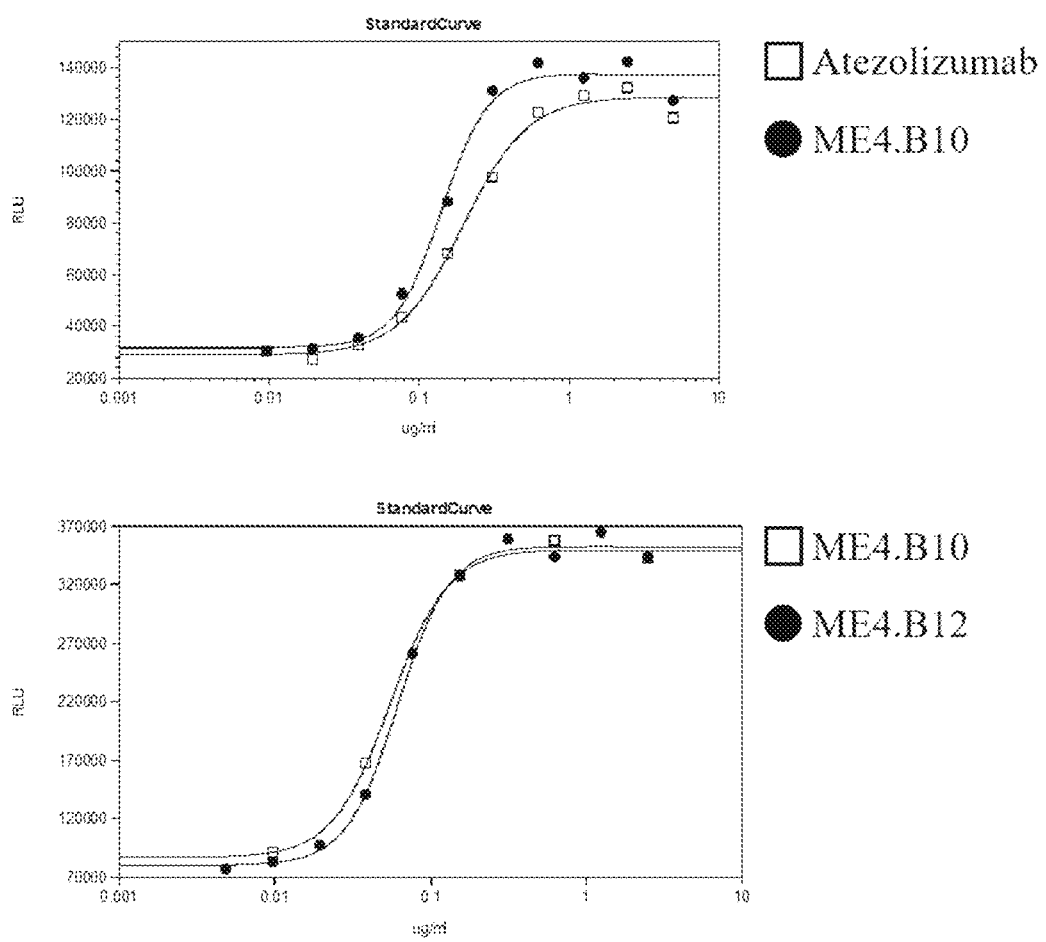

[Figure 10]
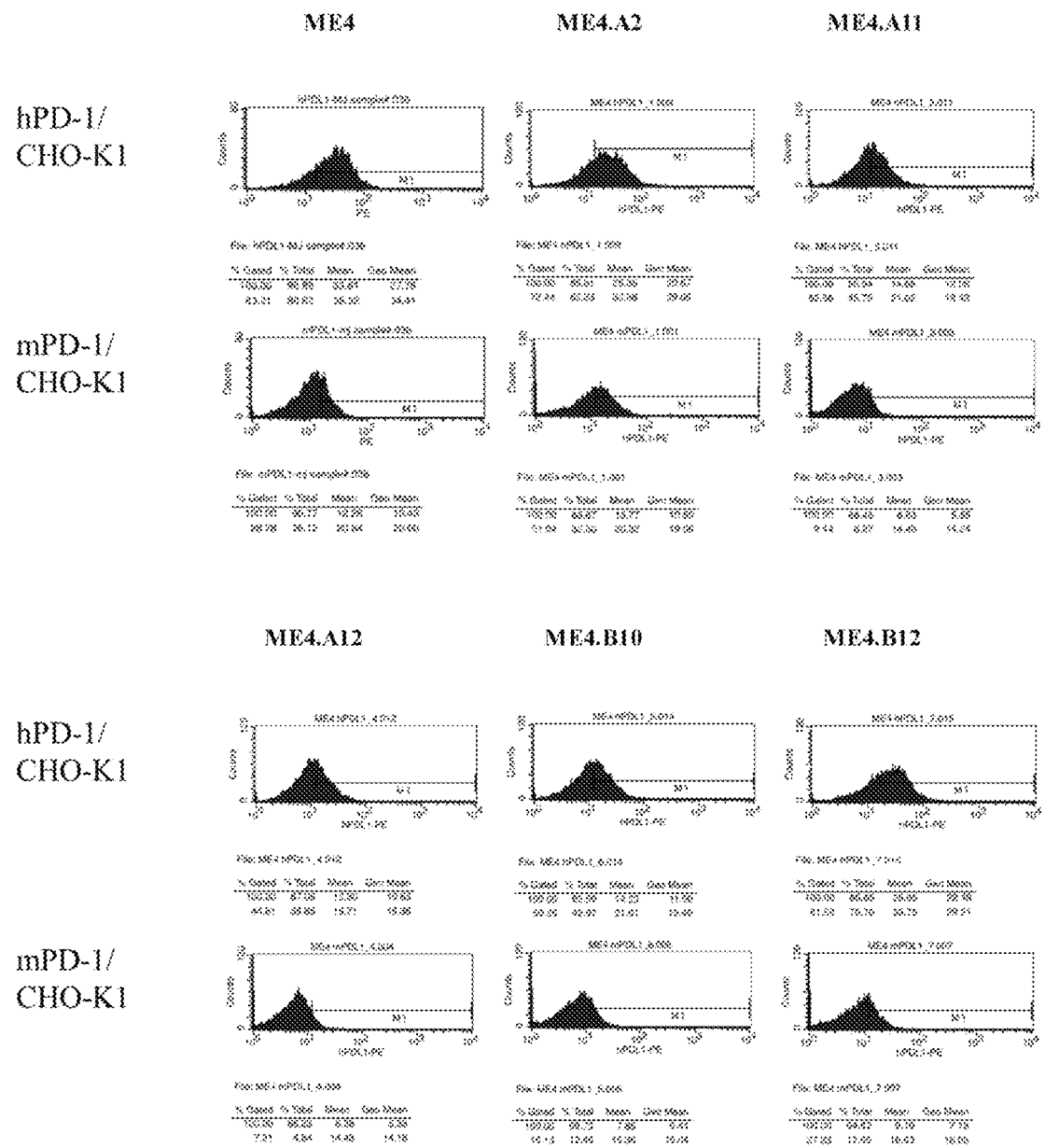

SEQUENCE LISTING

<160> NUMBER OF SEQ ID NOS: 30

<210> SEQ ID NO 1
<211> LENGTH: 8
<212> TYPE: PRT
<213> ORGANISM: Artificial Sequence
<220> FEATURE:
<223> OTHER INFORMATION: VH_CDR1 of 1G1

<400> SEQUENCE: 1

Gly Phe Thr Phe Asp Asp Tyr Ala
1               5

<210> SEQ ID NO 2
<211> LENGTH: 8
<212> TYPE: PRT
<213> ORGANISM: Artificial Sequence
<220> FEATURE:
<223> OTHER INFORMATION: VH_CDR2 of 1G1

<400> SEQUENCE: 2

Ile Ser Trp Asn Ser Gly Ser Ile

```
1               5

<210> SEQ ID NO 3
<211> LENGTH: 14
<212> TYPE: PRT
<213> ORGANISM: Artificial Sequence
<220> FEATURE:
<223> OTHER INFORMATION: VH_CDR3 of 1G1

<400> SEQUENCE: 3

Ala Lys Pro Arg Asp Ile Ser Ser Trp Leu Gly Met Asp Val
1               5                   10

<210> SEQ ID NO 4
<211> LENGTH: 6
<212> TYPE: PRT
<213> ORGANISM: Artificial Sequence
<220> FEATURE:
<223> OTHER INFORMATION: VL_CDR1 of 1G1

<400> SEQUENCE: 4

Gln Asp Ile Ser Ser Trp
1               5

<210> SEQ ID NO 5
<211> LENGTH: 3
<212> TYPE: PRT
<213> ORGANISM: Artificial Sequence
<220> FEATURE:
<223> OTHER INFORMATION: VL_CDR2 of 1G1

<400> SEQUENCE: 5

Ala Ala Ser
1

<210> SEQ ID NO 6
<211> LENGTH: 9
<212> TYPE: PRT
<213> ORGANISM: Artificial Sequence
<220> FEATURE:
<223> OTHER INFORMATION: VL_CDR3 of IG1

<400> SEQUENCE: 6

Gln Gln Thr Asn Asn Phe Pro Tyr Thr
1               5

<210> SEQ ID NO 7
<211> LENGTH: 8
<212> TYPE: PRT
<213> ORGANISM: Artificial Sequence
<220> FEATURE:
<223> OTHER INFORMATION: VH_CDR1 of ME4

<400> SEQUENCE: 7

Gly Gly Thr Phe Asn Asn Tyr Ala
1               5

<210> SEQ ID NO 8
<211> LENGTH: 8
<212> TYPE: PRT
<213> ORGANISM: Artificial Sequence
<220> FEATURE:
<223> OTHER INFORMATION: VH_CDR2 of ME4

<400> SEQUENCE: 8

Ile Ile Pro Ile Leu Gly Ile Ala
1               5
```

```
<210> SEQ ID NO 9
<211> LENGTH: 14
<212> TYPE: PRT
<213> ORGANISM: Artificial Sequence
<220> FEATURE:
<223> OTHER INFORMATION: VH_CDR3 of ME4

<400> SEQUENCE: 9

Ala Arg Ser Tyr Ser Gly Tyr Ala Glu Gly Ala Phe Asp Ile
1               5                   10

<210> SEQ ID NO 10
<211> LENGTH: 9
<212> TYPE: PRT
<213> ORGANISM: Artificial Sequence
<220> FEATURE:
<223> OTHER INFORMATION: VL_CDR1 of ME4

<400> SEQUENCE: 10

Ser Ser Asn Ile Gly Ala Gly Tyr Asp
1               5

<210> SEQ ID NO 11
<211> LENGTH: 3
<212> TYPE: PRT
<213> ORGANISM: Artificial Sequence
<220> FEATURE:
<223> OTHER INFORMATION: VL_CDR2 of ME4

<400> SEQUENCE: 11

Gly Asn Ser
1

<210> SEQ ID NO 12
<211> LENGTH: 11
<212> TYPE: PRT
<213> ORGANISM: Artificial Sequence
<220> FEATURE:
<223> OTHER INFORMATION: VL_CDR3 of ME4

<400> SEQUENCE: 12

Gln Ser Tyr Asp Ser Arg Leu Ser Gly Pro Val
1               5                   10

<210> SEQ ID NO 13
<211> LENGTH: 9
<212> TYPE: PRT
<213> ORGANISM: Artificial Sequence
<220> FEATURE:
<223> OTHER INFORMATION: VL_CDR3 of 1G1.D8

<400> SEQUENCE: 13

Gln Gln Thr Thr Asn Phe Pro Tyr Thr
1               5

<210> SEQ ID NO 14
<211> LENGTH: 9
<212> TYPE: PRT
<213> ORGANISM: Artificial Sequence
<220> FEATURE:
<223> OTHER INFORMATION: VL_CDR3 of 1G1.E12

<400> SEQUENCE: 14

Gln Gln Thr Val Thr Phe Pro Tyr Thr
1               5
```

<210> SEQ ID NO 15
<211> LENGTH: 14
<212> TYPE: PRT
<213> ORGANISM: Artificial Sequence
<220> FEATURE:
<223> OTHER INFORMATION: VH_CDR3 of ME4.A2

<400> SEQUENCE: 15

Ala Arg Ser Ser Arg Gly Tyr Ala His Gly Ala Phe Asp Ile
1               5                   10

<210> SEQ ID NO 16
<211> LENGTH: 14
<212> TYPE: PRT
<213> ORGANISM: Artificial Sequence
<220> FEATURE:
<223> OTHER INFORMATION: VH_CDR3 of ME4.A11

<400> SEQUENCE: 16

Ala Arg Ser Arg Gly Gly Tyr Ala His Gly Ala Phe Asp Ile
1               5                   10

<210> SEQ ID NO 17
<211> LENGTH: 14
<212> TYPE: PRT
<213> ORGANISM: Artificial Sequence
<220> FEATURE:
<223> OTHER INFORMATION: VH_CDR3 of ME4.A12

<400> SEQUENCE: 17

Ala Arg Ser His Trp Gly Tyr Ala His Gly Ala Phe Asp Ile
1               5                   10

<210> SEQ ID NO 18
<211> LENGTH: 14
<212> TYPE: PRT
<213> ORGANISM: Artificial Sequence
<220> FEATURE:
<223> OTHER INFORMATION: VH_CDR3 of ME4.B10

<400> SEQUENCE: 18

Ala Arg Ser Ala Arg Gly Tyr Ala His Gly Ala Phe Asp Ile
1               5                   10

<210> SEQ ID NO 19
<211> LENGTH: 14
<212> TYPE: PRT
<213> ORGANISM: Artificial Sequence
<220> FEATURE:
<223> OTHER INFORMATION: VH_CDR3 of ME4.B12

<400> SEQUENCE: 19

Ala Arg Ser Ser Phe Gly Tyr Ser Val Gly Ala Phe Asp Ile
1               5                   10

<210> SEQ ID NO 20
<211> LENGTH: 121
<212> TYPE: PRT
<213> ORGANISM: Artificial Sequence
<220> FEATURE:
<223> OTHER INFORMATION: VH of 1G1

<400> SEQUENCE: 20

Gln Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr 20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Lys Pro Arg Asp Ile Ser Ser Trp Leu Gly Met Asp Val Trp Gly
            100                 105                 110

Gln Gly Thr Thr Val Thr Val Ser Ser
        115                 120

<210> SEQ ID NO 21
<211> LENGTH: 108
<212> TYPE: PRT
<213> ORGANISM: Artificial Sequence
<220> FEATURE:
<223> OTHER INFORMATION: VL of 1G1

<400> SEQUENCE: 21

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Thr Asn Asn Phe Pro Tyr
                85                  90                  95

Thr Phe Gly Gln Gly Thr Lys Leu Glu Ile Lys Arg
            100                 105

<210> SEQ ID NO 22
<211> LENGTH: 108
<212> TYPE: PRT
<213> ORGANISM: Artificial Sequence
<220> FEATURE:
<223> OTHER INFORMATION: VL of 1G1.D8

<400> SEQUENCE: 22

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Thr Thr Asn Phe Pro Tyr
                85                  90                  95

Thr Phe Gly Gln Gly Thr Lys Leu Glu Ile Lys Arg
            100                 105

<210> SEQ ID NO 23
<211> LENGTH: 108
<212> TYPE: PRT
<213> ORGANISM: Artificial Sequence
<220> FEATURE:
<223> OTHER INFORMATION: VL of 1G1.E12

<400> SEQUENCE: 23

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Asp Ile Ser Ser Trp
            20                  25                  30

Leu Ala Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Ser Ala Thr Tyr Tyr Cys Gln Gln Thr Val Thr Phe Pro Tyr
                85                  90                  95

Thr Phe Gly Gln Gly Thr Lys Leu Glu Ile Lys Arg
            100                 105

<210> SEQ ID NO 24
<211> LENGTH: 121
<212> TYPE: PRT
<213> ORGANISM: Artificial Sequence
<220> FEATURE:
<223> OTHER INFORMATION: VH of ME4

<400> SEQUENCE: 24

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Val Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Thr Phe
    50                  55                  60

Gln Gly Arg Val Thr Ile Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Tyr Ser Gly Tyr Ala Glu Gly Ala Phe Asp Ile Trp Gly
            100                 105                 110

Gln Gly Thr Met Val Thr Val Ser Ser
        115                 120

<210> SEQ ID NO 25
<211> LENGTH: 112
<212> TYPE: PRT
<213> ORGANISM: Artificial Sequence
<220> FEATURE:
<223> OTHER INFORMATION: VL of ME4

<400> SEQUENCE: 25

Gln Phe Val Leu Thr Gln Pro Pro Ser Val Ser Gly Ala Pro Gly Gln

```
                1               5                   10                  15
            Arg Val Thr Ile Ser Cys Thr Gly Ser Ser Asn Ile Gly Ala Gly
                            20                  25                  30
            Tyr Asp Val His Trp Tyr Gln Gln Leu Pro Gly Thr Ala Pro Lys Val
                        35                  40                  45
            Leu Ile Tyr Gly Asn Ser Asp Arg Pro Ser Gly Val Pro Asp Arg Phe
                    50                  55                  60
            Ser Gly Ser Lys Ser Gly Thr Ser Ala Ser Leu Ala Ile Thr Gly Leu
            65                  70                  75                  80
            Gln Gly Glu Asp Lys Ala Thr Tyr Tyr Cys Gln Ser Tyr Asp Ser Arg
                            85                  90                  95
            Leu Ser Gly Pro Val Phe Gly Thr Gly Thr Lys Val Thr Val Leu Gly
                        100                 105                 110

<210> SEQ ID NO 26
<211> LENGTH: 121
<212> TYPE: PRT
<213> ORGANISM: Artificial Sequence
<220> FEATURE:
<223> OTHER INFORMATION: VH of ME4.A2

<400> SEQUENCE: 26

Gln Val Gln Leu Val Glu Ser Gly Ala Glu Val Lys Lys Pro Gly Ser
            1               5                   10                  15
            Ser Val Lys Val Ser Cys Lys Ala Ser Gly Gly Thr Phe Asn Asn Tyr
                            20                  25                  30
            Ala Val Ser Trp Val Arg Gln Ala Pro Gly Gln Gly Leu Glu Trp Met
                        35                  40                  45
            Gly Arg Ile Ile Pro Ile Leu Gly Ile Ala Asn Tyr Ala Gln Thr Phe
                    50                  55                  60
            Gln Gly Arg Val Thr Ile Thr Ala Asp Lys Ser Thr Thr Thr Ala Tyr
            65                  70                  75                  80
            Met Glu Leu Ser Ser Leu Arg Ser Glu Asp Thr Ala Val Tyr Tyr Cys
                            85                  90                  95
            Ala Arg Ser Ser Arg Gly Tyr Ala His Gly Ala Phe Asp Ile Trp Gly
                        100                 105                 110
            Gln Gly Thr Met Val Thr Val Ser Ser
                    115                 120

<210> SEQ ID NO 27
<211> LENGTH: 121
<212> TYPE: PRT
<213> ORGANISM: Artificial Sequence
<220> FEATURE:
<223> OTHER INFORMATION: VH of ME4.A11

<400> SEQUENCE: 27

Gln Val Gln Leu Val Glu Ser Gly Ala Glu Val Lys Lys Pro Gly Ser
            1               5                   10                  15
            Ser Val Lys Val Ser Cys Lys Ala Ser Gly Gly Thr Phe Asn Asn Tyr
                            20                  25                  30
            Ala Val Ser Trp Val Arg Gln Ala Pro Gly Gln Gly Leu Glu Trp Met
                        35                  40                  45
            Gly Arg Ile Ile Pro Ile Leu Gly Ile Ala Asn Tyr Ala Gln Thr Phe
                    50                  55                  60
            Gln Gly Arg Val Thr Ile Thr Ala Asp Lys Ser Thr Thr Thr Ala Tyr
            65                  70                  75                  80
```

Met Glu Leu Ser Ser Leu Arg Ser Glu Asp Thr Ala Val Tyr Tyr Cys
                85                  90                  95

Ala Arg Ser Arg Gly Gly Tyr Ala His Gly Ala Phe Asp Ile Trp Gly
            100                 105                 110

Gln Gly Thr Met Val Thr Val Ser Ser
        115                 120

<210> SEQ ID NO 28
<211> LENGTH: 121
<212> TYPE: PRT
<213> ORGANISM: Artificial Sequence
<220> FEATURE:
<223> OTHER INFORMATION: VH of ME4.A12

<400> SEQUENCE: 28

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Val Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Thr Phe
    50                  55                  60

Gln Gly Arg Val Thr Ile Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser His Trp Gly Tyr Ala His Gly Ala Phe Asp Ile Trp Gly
            100                 105                 110

Gln Gly Thr Met Val Thr Val Ser Ser
        115                 120

<210> SEQ ID NO 29
<211> LENGTH: 121
<212> TYPE: PRT
<213> ORGANISM: Artificial Sequence
<220> FEATURE:
<223> OTHER INFORMATION: VH of ME4.B10

<400> SEQUENCE: 29

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Val Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Thr Phe
    50                  55                  60

Gln Gly Arg Val Thr Ile Thr Ala Asp Lys Ser Thr Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ala Arg Gly Tyr Ala His Gly Ala Phe Asp Ile Trp Gly
            100                 105                 110

Gln Gly Thr Met Val Thr Val Ser Ser
        115                 120

<210> SEQ ID NO 30

```
<211> LENGTH: 121
<212> TYPE: PRT
<213> ORGANISM: Artificial Sequence
<220> FEATURE:
<223> OTHER INFORMATION: VH of ME4.B12

<400> SEQUENCE: 30

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Asn Asn Tyr
            20                  25                  30

Ala Val Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Thr Phe
    50                  55                  60

Gln Gly Arg Val Thr Ile Thr Ala Asp Lys Ser Thr Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Ser Phe Gly Tyr Ser Val Gly Ala Phe Asp Ile Trp Gly
            100                 105                 110

Gln Gly Thr Met Val Thr Val Ser Ser
            115                 120
```

ANTI-PD-L1 ANTIBODY AND USE THEREOF

RELATED APPLICATIONS

This application is a US National stage entry of International Application No. PCT/KR2018/016715, which designated the United States and was filed on Dec. 27, 2018, published in Korean.

This application claims priority under 35 U.S.C. § 119 or 365 to KR, Application No. 10-2017-0180440, filed Dec. 27, 2017. The entire teachings of the above applications are incorporated herein by reference.

BACKGROUND OF THE INVENTION

Field of the Invention

The present invention relates to an anti-PD-L1 antibody or an antigen-binding fragment thereof, a nucleic acid encoding the same, a vector including the nucleic acid, a cell transformed with the vector, a method for producing the antibody or an antigen-binding fragment thereof, a pharmaceutical composition for preventing or treating cancer comprising the same, and a composition for co-administration with an antibody other than an antibody binding to PD-L1, comprising the same.

Description of the Related Art

An immune system has a physiological function of protecting subjects from infectious pathogens and non-infectious foreign matter. Cancer cells also express cancer-specific antigens and thus are recognized as non-self cells, and should be removed by the immune system. However, the immune system does not suppress tumor growth in a variety of types of cancer, and the cancer tends to worsen. This is because cancer cells have various means to actively evade the immune response. Among them, an immune checkpoint is attracting much attention in tumor immunology at present.

The activation of T cells is performed using two signals. Primarily, MHC on antigen-presenting cells (APCs) binds to T-cell receptors (TCRs) on T cells, and transfers an activation signal through the interaction between CD3 and ζ in the TCR complex. Independently therefrom, binding between the receptor on the T cells and the ligand on the APC is required, and a typical example thereof is a CD28/CD80 interaction. When CD28 on T cells binds to CD80 present on the surface of APCs (such as dendritic cells, macrophages and B cells), expression of proteins such as anti-apoptotic proteins, growth factors and cytokines is induced in T cells, thus causing activation of the T cells through proliferation and differentiation of T cells. In addition to CD28/CD80, there are a number of receptors/ligands having these functions, such as 4-1BB/4-1BBL and OX40/OX40-L, and these are called "co-stimulatory factors". On the other hand, there are also molecules called "co-inhibitory factors" that inhibit the activity of T cells by binding of receptors on T cells to ligands on APCs, and known typical examples thereof include CTLA-4/CD80, PD-1/PD-L1, Galectin-9/TIM-3 and the like. Through them, T cells regulate immune responses and immune tolerance.

The PD-1/PD-L1 signaling system has been reported as a typical example of a co-inhibitory signal. PD-1 is known to be mainly expressed in activated CD4+/CD8+ T cells and B cells and to be mainly involved in the late immune response (*EMBO J.* 11: 3887-95. 1992.). The binding between PD-1 and the ligand thereof, PD-L1/L2, recruits SHP-2, which is a type of phosphatase, to suppress proteins and phosphatases associated with the activation of T cells, and suppress cytotoxicity-related activity such as proliferation of T cells and production of interferon-gamma (interferon-γ) (*J. Exp. Med.* 209: 1201-17. 2012.). In particular, it is known that cancer cells also express PD-L1 to thus inhibit immune activity through interaction with T cells, which has a great effect on immune response evasion of cancer (*Sci. Rep.* 5: 13110. 2015.). For example, when the PD-1-suppressing antibody, Keytruda® (component name: pembrolizumab) developed by Merck is administered as a primary therapeutic agent to patients with metastatic non-small cell lung cancer, it is administered only to patients having a PD-L1-expressing tumor proportional score (TPS) of 50% or more, determined through companion diagnosis. In this case, it has been reported that the median progression-free survival, which is an indicator of tumor suppression efficacy, is significantly increased to 10.3 months, compared to 6.0 months for the conventional therapeutic agent (Keynote-024). However, in the case of Opdivo® (component name: nivolumab) developed by BMS, which is a PD-1 inhibitory antibody having the same mechanism, patients were selected and clinically tested, regardless of whether or not PD-L1 was expressed. However, product approval could not be obtained due to almost nonexistent or poor efficacy. This is presumed to be due to the fact that only 30% of patients have a high PD-L1 expression tumor proportion score (TPS>50%), and thus the number of patients exhibiting efficacy is small compared to the total number of patients tested. That is, PD-L1 expression of the tumor is essential for inhibition of tumor growth through inhibition of PD-1/PD-L1 signals.

Under these backgrounds, PD-L1-inhibiting antibodies have recently been approved sequentially. Roche's Tecentriq® (component name: atezolizumab) is a first-in-class drug which was approved and for which the range of indications is expanding, with regard to bladder cancer and non-small cell lung cancer. As second movers, Pfizer's Bavencio® (component name: avelumab) and AstraZeneca's Imfinzi® (component name: durvalumab) are also expanding indications, starting with bladder cancer.

Based on this technical background, the present inventors developed a novel anti-PD-L1 antibody that is distinguished from a conventional anti-PD-L1 antibody, and completed the present invention by improving the binding ability and function as an immune anticancer agent through an optimization process.

SUMMARY OF THE INVENTION

Therefore, the present invention has been made in view of the above problems and it is one object of the present invention to provide a novel antibody to PD-L1 or an antigen-binding fragment thereof.

It is another object of the present invention to provide a nucleic acid encoding the antibody or an antigen-binding fragment thereof.

It is another object of the present invention to provide a vector including the nucleic acid, a cell transformed with the vector, and a method for producing the antibody or antigen-binding fragment thereof.

It is another object of the present invention to provide a composition for treating a tumor comprising the antibody or an antigen-binding fragment thereof.

It is another object of the present invention to provide a composition for co-administration with another antibody, comprising the antibody or an antigen-binding fragment thereof.

In accordance with one aspect of the present invention, the above and other objects can be accomplished by the provision of an antibody binding to PD-L1 or an antigen-binding fragment thereof, including a heavy-chain variable region comprising a heavy-chain CDR1 of SEQ ID NO: 1 or 7, a heavy-chain CDR2 of SEQ ID NO: 2 or 8, and a heavy-chain CDR3 selected from the group consisting of SEQ ID NOS: 3, 9, 15, 16, 17, 18 and 19, and a light-chain variable region comprising a light-chain CDR1 of SEQ ID NO: 4 or 10, a light-chain CDR2 of SEQ ID NO: 5 or 11, and a light-chain CDR3 selected from the group consisting of SEQ ID NOS: 6, 12, 13 and 4.

In another aspect of the present invention, provided is a nucleic acid encoding the antibody or an antigen-binding fragment thereof.

In another aspect of the present invention, provided is a vector including the nucleic acid.

In another aspect of the present invention, provided is a cell transformed with the vector.

In another aspect of the present invention, provided is a method for producing the antibody or an antigen-binding fragment thereof, including (a) culturing the cell and (b) recovering the antibody or antigen-binding fragment thereof from the cultured cell.

In another aspect of the present invention, provided is a composition for treating a tumor comprising the antibody or antigen-binding fragment thereof as an active ingredient. In another aspect of the present invention, provided is a method of preventing or treating a tumor comprising administering the antibody or antigen-binding fragment thereof to a patient with a tumor. In another aspect of the present invention, provided are the use of the antibody or antigen-binding fragment thereof for the inhibition of the immunosuppressive mechanism of PD-L1 and the use of the antibody or antigen-binding fragment thereof for the prevention or treatment of a tumor.

In another aspect of the present invention, provided is a composition for co-administration with an antibody other than an antibody binding to PD-L1, the composition comprising the antibody or antigen-binding fragment thereof. In another aspect of the present invention, provided is a method of preventing or treating a tumor, the method including administering the antibody or an antigen-binding fragment thereof in combination with an antibody other than an antibody binding to PD-L1 to a patient. In another aspect of the present invention, provided are the use of the antibody or antigen-binding fragment thereof for co-administration with an antibody other than an antibody binding to PD-L1 to treat a tumor.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows the result of confirmation as to whether binding occurs when reacting a monoclonal scFv phage with a CHO-K1 cell line overexpressing human or mouse PD-L1;

FIG. 2 shows the result of evaluation of the inhibitory effect of the PD-1/PD-L1 signal of each clone in a screening process of an anti-PD-L1 antibody;

FIG. 3 shows the result of SDS-PAGE under reducing and non-reducing conditions with regard to a product obtained after transient expression and purification of the selected anti-PD-L1 antibody;

FIG. 4 shows the result of ELISA for evaluating the binding of the transiently expressed and purified anti-PD-L1 antibody to human and mouse PD-L1;

FIG. 5 shows the result of flow cytometry for evaluating the binding of the transiently expressed and purified anti-PD-L1 antibody to human and mouse PD-L1-expressing cells;

FIG. 6 shows the result of evaluation of the effect of inhibiting PD-1/PD-L1 signals of the transiently expressed and purified anti-PD-L1 antibody;

FIG. 7 shows the result of evaluation of the anti-cancer efficacy of the selected anti-PD-L1 antibody in a MC38 tumor mouse model;

FIG. 8 shows the result of comparison in the PD-1/PD-L1 signal inhibition efficacy between clones before optimization and antibody clones imparted with improved affinity by performing antibody optimization;

FIG. 9 shows the result of measurement of the concentration dependency of PD-1/PD-L1 signal inhibition efficacy of the selected optimized antibody; and FIG. 10 shows the result of flow cytometry of evaluation of the binding of the selected opted antibody to human and mouse PD-L1-expressing cells.

DETAILED DESCRIPTION OF THE INVENTION

Unless defined otherwise, all technical and scientific terms used herein have the same meanings as appreciated by those skilled in the field to which the present invention pertains. In general, the nomenclature used herein is well-known in the art and is ordinarily used.

In one aspect, the present invention is directed to an antibody binding to PD-L1 or an antigen-binding fragment thereof, comprising a heavy-chain variable region including a heavy-chain CDR1 of SEQ ID NO: 1 or 7, a heavy-chain CDR2 of SEQ ID NO: 2 or 8, and a heavy-chain CDR3 selected from the group consisting of SEQ ID NOS: 3, 9, 15, 16, 17, 18 and 19, and a light-chain variable region comprising a light-chain CDR1 of SEQ ID NO: 4 or 10, a light-chain CDR2 of SEQ ID NO: 5 or 11, and a light-chain CDR3 selected from the group consisting of SEQ ID NOS: 6, 12, 13 and 14.

As used herein, the term "antibody" refers to an anti-PD-L1 antibody that specifically binds to PD-L1. The scope of the present invention includes not only a complete antibody specifically binding to PD-L1 but also an antigen-binding fragment of the antibody molecule.

The term "complete antibody" refers to a structure having two full-length light chains and two full-length heavy chains, wherein each light chain is linked to a corresponding heavy chain by a disulfide bond. The complete antibody includes subtypes of IgA, IgD, IgE, IgM and IgG, in particular IgG includes IgG1, IgG2, IgG3 and IgG4. The heavy-chain constant region has gamma ($\gamma$), mu ($\mu$), alpha ($\alpha$), delta ($\delta$) and epsilon ($\epsilon$) types, and is subclassified into gamma 1 ($\gamma$1), gamma 2 ($\gamma$2), gamma 3 ($\gamma$3), gamma 4 ($\gamma$4), alpha 1 ($\alpha$1) and alpha 2 ($\alpha$2). The light-chain constant region has kappa ($\kappa$) and lambda ($\lambda$) types.

The antigen-binding fragment of an antibody or antibody fragment is a fragment that has antigen-binding capacity and includes Fab, F(ab'), F(ab')2, Fv and the like. Among the antibody fragments, Fab refers to a structure including a variable region of each of the heavy chain and the light chain, the constant region of the light chain, and the first constant domain (CH1) of the heavy chain, each having one antigen-binding site. Fab' is different from Fab in that it further includes a hinge region including at least one cysteine residue at the C-terminus of the CH1 domain of the heavy chain. F(ab')2 is created by a disulfide bond between cysteine residues in the hinge region of Fab'. Fv is the minimal antibody fragment having only a heavy-chain variable region and a light-chain variable region, and recombinant technology for producing Fv disclosed in PCT International Publications such as WO 88/10649, WO 88/106630, WO 88/07085, WO 88/07086 and WO 88/09344. Two-chain Fv is a fragment wherein the variable region of the heavy chain and the variable region of the light chain are linked by a non-covalent bond, and single-chain Fv (scFv) is a fragment wherein the variable region of the heavy chain and the variable region of the light chain are generally linked by a covalent bond via a peptide linker therebetween, or are directly linked at the C-terminal, forming a dimer-shaped structure, like the two-chain Fv. Such antibody fragments may be obtained using proteases (e.g., Fab can be obtained by restriction-cleaving the complete antibody with papain, and the F(ab')2 fragment can be obtained by restriction-cleaving the complete antibody with pepsin), and may be prepared using genetic recombination techniques.

In one embodiment, the antibody of the present invention is in an Fv form (for example, scFv) or a complete antibody form. In addition, the heavy-chain constant region may be selected from gamma (γ), mu (μ), alpha (α), delta (δ) and epsilon (ε) isotypes. For example, the constant region may be gamma 1 (IgG1), gamma 3 (IgG3) or gamma 4 (IgG4). The light-chain constant region may be kappa or lambda.

As used herein, the term "heavy chain" encompasses both a full-length heavy chain, which includes a variable domain (VH) containing an amino acid sequence having a variable region sequence sufficient for imparting specificity to an antigen and three constant domains (CH1, CH2 and CR3), and a fragment thereof. As used herein, the term "light chain" encompasses both a full-length light chain, which includes a variable domain (VL) containing an amino acid sequence having a variable region sequence sufficient for imparting specificity to an antigen and a constant domain (CL), and a fragment thereof.

The antibody of the present invention includes, but is not limited to, monoclonal antibodies, multispecific antibodies, human antibodies, humanized antibodies, chimeric antibodies, scFVs, Fab fragments, F(ab')2 fragments, disulfide-bond Fvs (sdFVs), anti-idiotypic (anti-Id) antibodies, epitope-binding fragments of such antibodies, and the like.

The term "monoclonal antibody" refers to an identical antibody, which is obtained from a population of substantially homogeneous antibodies, that is, each antibody constituting the population, excluding possible naturally occurring mutations that may be present in trivial amounts. Monoclonal antibodies are highly specific and are thus induced against a single antigenic site. Unlike conventional (polyclonal) antibody preparations that typically include different antibodies directed against different determinants (epitopes), each monoclonal antibody is directed against a single determinant on the antigen.

The term "epitope" refers to a protein determinant to which an antibody can specifically bind. Epitopes usually consist of a group of chemically active surface molecules, such as amino acid or sugar side chains, and generally have not only specific three-dimensional structural characteristics but also specific charge characteristics. Three-dimensional epitopes are distinguished from non-three-dimensional epitopes in that a bond to the former is broken in the presence of a denatured solvent, while a bond to the latter is not broken.

The non-human (e.g., murine) antibody of the "humanized" form is a chimeric antibody containing a minimal sequence derived from non-human immunoglobulin. In most cases, the humanized antibody a human immunoglobulin (receptor antibody) in which a residue from the hypervariable region of a receptor is replaced with a residue from the hypervariable region of a non-human species (donor antibody) such as a mouse, rat, rabbit or non-human primate having the desired specificity, affinity and ability.

As used herein, the term "human antibody" refers to a molecule derived from human immunoglobulin, in which all of the amino acid sequences constituting the antibody including a complementarity-determining region and a structural region are composed of human immunoglobulins.

A part of the heavy chain and/or light chain is identical to or homologous with the corresponding sequence in an antibody derived from a particular species or belonging to a particular antibody class or subclass, while the remaining chain(s) includes "chimeric" antibodies (immunoglobulins) which are identical to or homologous with corresponding sequences in an antibody derived from another species or belonging to another antibody class or subclass, as well as fragments of such antibody exhibiting the desired biological activity.

As used herein, the term "antibody variable domain" refers to the light- and heavy-chain regions of an antibody molecule including the amino acid sequences of a complementarity-determining region (CDR; i.e., CDR1, CDR2, and CDR3) and a framework region (FR). VH refers to a variable domain of the heavy chain. VL refers to a variable domain of the light chain.

The term "complementarity-determining region" (CDR) refers to an amino acid residue of the antibody variable domain, which is necessary for antigen binding. Each variable domain typically has three CDR regions, identified as CDR1, CDR2, and CDR3.

The anti-PD-L1 antibody or an antigen-binding fragment thereof according to the present invention includes, for example:

a heavy-chain variable region including a heavy-chain CDR1 of SEQ ID NO: 1, a heavy-chain CDR2 of SEQ ID NO: 2, and a heavy-chain CDR3 of SEQ ID NO: 3, and a light-chain variable region including a light-chain CDR1 SEQ ID NO: 4, a light-chain CDR2 of SEQ ID NO: 5, and a light-chain CDR3 of SEQ ID NO: 6;

a heavy-chain variable region including a heavy-chain CDR1 of SEQ ID NO: 1, a heavy-chain CDR2 of SEQ ID NO: 2, and a heavy-chain CDR3 of SEQ ID NO: 3, and a light-chain variable region including a light-chain CDR1 of SEQ ID NO: 4, a light-chain CDR2 of SEQ ID NO: 5, and a light-chain CDR3 of SEQ ID NO: 13;

a heavy-chain variable region including a heavy-chain CDR1 of SEQ ID NO: 1, a heavy-chain CDR2 of SEQ ID NO: 2, and a heavy-chain CDR3 of SEQ ID NO: 3, and a light-chain variable region including a light-chain CDR1 SEQ ID NO: 4, a light-chain CDR2 of SEQ ID NO: 5, and a light-chain CDR3 of SEQ ID NO: 14;

a heavy-chain variable region including a heavy-chain CDR1 of SEQ ID NO: 7, a heavy-chain CDR2 of SEQ ID NO: 8, and a heavy-chain CDR3 of SEQ ID NO: 9, and a light-chain variable region including a light-chain CDR1 of SEQ ID NO: 10, a light-chain CDR2 of SEQ ID NO: 11, and a light-chain CDR3 of SEQ ID NO: 12;

heavy-chain variable region including a heavy-chain CDR1 of SEQ ID NO: 7, a heavy-chain CDR2 of SEQ ID NO: 8, and a heavy-chain CDR3 SEQ ID NO: 15, and a light-chain variable region including a light-chain CDR1 of SEQ ID NO: 10, a light-chain CDR2 of SEQ ID NO: 11, and a light-chain CDR3 of SEQ ID NO: 12;

a heavy-chain variable region including a heavy-chain CDR1 of SEQ ID NO: 7, a heavy-chain CDR2 of SEQ ID NO: 8, and a heavy-chain CDR3 of SEQ ID NO: 16, and a light-chain variable region including a light-chain CDR1 of SEQ ID NO: 10, a light-chain CDR2 of SEQ ID NO: 11, and a light-chain CDR3 of SEQ ID NO: 12;

a heavy-chain variable region including a heavy-chain CDR1 of SEQ ID NO: 7, a heavy-chain CDR2 of SEQ ID NO: 8, and a heavy-chain CDR3 of SEQ ID NO: 17, and a light-chain variable region including a light-chain CDR1 of SEQ ID NO: 10, a light-chain CDR2 of SEQ ID NO: 11, and a light-chain CDR3 of SEQ ID NO: 12;

a heavy-chain variable region including a heavy-chain CDR1 of SEQ ID NO: 7, a heavy-chain CDR2 of SEQ ID NO: 8, and a heavy-chain CDR3 of SEQ TD NO: 18, and a light-chain variable region including a light-chain CDR1 of SEQ ID NO: 10, a light-chain CDR2 of SEC ID NO: 11, and a light-chain CDR3 of SEQ ID NO: 12; and a heavy-chain variable region including a heavy-chain CDR1 of SEQ ID NO: 7, a heavy-chain CDR2 of SEQ ID NO: 8, and a heavy-chain CDR3 of SEQ ID NO: 19, and a light-chain variable region including a light-chain CDR1 of SEQ ID NO: 10, a light-chain CDR2 of SEQ ID NO: 11, and a light-chain CDR3 of SEQ ID NO: 12.

The term "framework region" (FR) refers to a variable domain residue other than a CDR residue. Each variable domain typically has four FRs, identified as FR1, FR2, FR3, and FR4.

The "Fv" fragment is an antibody fragment containing complete antibody recognition and binding sites. Such a region includes a dimer that consists of one heavy-chain variable domain and one light-chain variable domain substantially tightly covalently connected to each other.

A "Fab" fragment contains variable domain and a constant domain of the light chain and a variable domain and a first constant domain (CH1) of the heavy chain. A F(ab')2 antibody fragment generally includes a pair of Fab fragments covalently linked via cysteine of a hinge region present at the C-terminal of the Fab' fragment.

The "single chain Fv (scFv)" antibody fragment has a single polypeptide chain including VH and VL domains of the antibody. The scFv may further include a polypeptide linker between the VH domain and the VL domain in order for the scFv to form a desired structure for antigen binding.

The anti-PD-L1 antibody may include single or double chains. Functionally, the binding affinity of the anti-PD-L1 antibody ranges from $10^{-5}$ M to $10^{-12}$ M. For example, the binding affinity of the anti-PD-L1 antibody is $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-5}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M or $10^{-5}$ M to $10^{-6}$ M.

The antibody binding to PD-L1 or an antigen-binding fragment thereof may include a heavy-chain variable region selected from the group consisting of SEQ ID NOS: 20, 24, 26, 27, 28, 29 and 30. In addition, the antibody binding to PD-L1 or an antigen-binding fragment thereof may include a light-chain variable region selected from the group consisting of SEQ ID NOS: 21, 22, 23 and 25.

In a specific embodiment according to the present invention, the antibody binding to PD-L1 or the antigen-binding fragment thereof may include:

the heavy-chain variable region of SEQ ID NO: 20 and the light-chain variable region of SEQ ID NO: 21;
the heavy-chain variable region of SEQ ID NO: 20 and the light-chain variable region of SEQ ID NO: 22;
the heavy-chain variable region of SEQ ID NO: 20 and the light-chain variable region of SEQ ID NO: 23;
the heavy-chain variable region of SEQ ID NO: 24 and the light-chain variable region of SEQ ID NO: 25;
the heavy-chain variable region of SEQ ID NO: 26 and the light-chain variable region of SEQ ID NO: 25;
the heavy-chain variable region of SEQ ID NO: 27 and the light-chain variable region of SEQ ID NO: 25;
the heavy-chain variable region of SEQ ID NO: 28 and the light-chain variable region of SEQ ID NO: 25;
the heavy-chain variable region of SEQ ID NO: 29 and the light-chain variable region of SEQ ID NO: 25; or
the heavy-chain variable region of SEQ ID NO: 30 and the light-chain variable region of SEQ ID NO: 25.

"Phage display" is a technique for displaying a mutant polypeptide as a fusion protein with at least a part of a coat protein on the surface of the particle of a phage, for example a fibrous phage. The usefulness of phage display is to rapidly and efficiently classify sequences that bind to target antigens with high affinity in large libraries of randomized protein mutants. Displaying peptides and protein libraries on phages has been used to screen millions of polypeptides in order to identify polypeptides with specific binding properties.

Phage display technology has offered a powerful tool for producing and screening novel proteins that bind to specific ligands (e.g., antigens). Using phage display technology, large libraries of protein mutants can be generated, and sequences binding with high affinity to target antigens can be rapidly classified. The nucleic acid encoding mutant polypeptides is fused with a nucleic acid sequence encoding a viral coat protein, e.g., a gene III or gene VIII protein. A monophasic phage display system, in which a nucleic acid sequence encoding a protein or polypeptide is fused with a nucleic acid sequence encoding a part of the gene III protein, has been developed. In the monophasic display system, a fused gene is expressed at a low level, and a wild-type gene III protein is also expressed, and thus particle infectivity is maintained.

It is important to demonstrate the expression of peptides on the fibrous phage surface and the expression of functional antibody fragments in the peripheral cytoplasm of E. coli for the development of antibody phage display libraries. Libraries of antibody- or antigen-binding polypeptides are produced through a number of methods, for example, methods of modifying a single gene by inserting a random DNA sequence or cloning a related gene sequence. Libraries can be screened regarding the expression of antibody- or antigen-binding proteins having desired characteristics.

Phage display technology has several advantages over conventional hybridomas and recombinant methods for producing antibodies having desired characteristics. This technique provides the generation of large antibody libraries with a variety of sequences within a short time without using animals. The production of hybridomas and the production of humanized antibodies may require a production time of several months. In addition, since no immunity is required, the phage antibody libraries can generate antibodies against antigens that are toxic or have low antigenicity. The phage antibody libraries can also be used to produce and identify novel therapeutic antibodies.

Techniques for generating human antibodies from immunized or non-immunized human, germline sequences, or naive B cell Ig repertoires using phage display libraries can be used. Naive or non-immunogenic antigen-binding libraries can be produced using various lymphatic tissues.

Techniques for identifying and separating high-affinity antibodies from phage display libraries are important for the separation of new therapeutic antibodies. The separation of high-affinity antibodies from the libraries depends on the size of the libraries, the production efficiency in bacterial cells and the variety of libraries. The size of the libraries is reduced by improper folding of the antibody- or antigen-binding protein and inefficient production due to the presence of the stop codon. Expression in bacterial cells may be inhibited by improper folding of the antibody- or antigen-binding domain. The expression can be improved by alternately mutating residues on the surface of the variable/constant interfaces or the selected CDR residues. The sequence of the framework region is an element that enables proper folding when generating antibody phage libraries in bacterial cells.

It is important to generate various libraries of antibody- or antigen-binding proteins in the separation of high-affinity antibodies. CDR3 regions have often been found to participate in antigen binding. Since the CDR3 region in the heavy chain varies considerably in terms of size, sequence and structural/dimensional morphology, various libraries can be produced using the same.

Also, diversity can be created by randomizing the CDR regions of variable heavy and light chains using all 20 amino acids at each position. The use of all 20 amino acids results in the production of antibody sequences having increased diversity and an increased chance of identifying new antibodies.

The antibody or antibody fragment of the present invention may include the sequence of the anti-PD-L1 antibody mentioned herein as well as biological equivalents thereto, as long as it can specifically recognize PD-L1. For example, additional variations can be made to the amino acid sequence of the antibody in order to further improve the binding affinity and/or other biological properties of the antibody. Such variations include, for example, deletion, insertion and/or substitution of the amino acid sequence residues of the antibody. Such amino acid variations are based on the relative similarity of amino acid side chain substituents, such as the hydrophobicity, hydrophilicity, charge and size thereof. It can be seen through analysis of the size, shape and type of amino acid side chain substituents that all of arginine, lysine and histidine are positively charged residues; alanine, glycine and serine have similar sizes; and phenylalanine, tryptophan and tyrosine have similar shapes. Thus, based on these considerations, arginine, lysine and histidine; alanine, glycine and serine; and phenylalanine, tryptophan and tyrosine are considered to be biologically functional equivalents.

When taking into consideration variations having biologically equivalent activity, the antibody or a nucleotide molecule encoding the same according to the present invention is interpreted to include a sequence having substantial identity with the sequence set forth in the sequence number. The term "substantial identity" means that a sequence has a homology of at least 90%, most preferably a homology of at least 95%, at least 96%, at least 97%, at least 98% or at least 99%, when aligning the sequence of the present invention with any other sequence so as to correspond to each other as closely as possible and analyzing the aligned sequence using algorithms commonly used in the art. Alignment methods for sequence comparison are well-known in the art. The NCBI Basic Local Alignment Search Tool (BLAST) is accessible through NCBI or the like, and can be used in conjunction with sequence analysis programs such as BLASTP, BLASTM, BLASTX, TBLASTN and TBLASTX over the Internet. BLAST is available at www.ncbi.nlm.nih.gov/BLAST/. A method of comparing sequence homology using this program can be found at www.ncbi.nlm.nih.gov/BLAST/blast_help.html.

Based on this, the antibody or antigen-binding fragment thereof according to the present invention can have a homology of 90%, 91%, 92%, 93%, 94%, 95%, 96%, 97%, 98%, 99%, or more compared to the sequence disclosed herein or the entirety thereof. Homology can be determined through sequence comparison and/or alignment by methods known in the art. For example, the percentage sequence homology of the nucleic acid or protein according to the present invention can be determined using a sequence comparison algorithm (i.e., BLAST or BLAST 2.0), manual alignment, or visual inspection.

In another aspect, the present invention is directed to a nucleic acid encoding the antibody or an antigen-binding fragment thereof.

By isolating the nucleic acid encoding the antibody or antigen-binding fragment thereof according to the present invention, an antibody or antigen-binding fragment thereof can be produced in a recombinant manner. The nucleic acid is isolated and inserted into a replicable vector, followed by further cloning (amplification of DNA) or further expression. Based on this, in another aspect, the present invention is directed to a vector including the nucleic acid.

The term "nucleic acid" is intended to encompass both DNA (gDNA and cDNA) and RNA molecules, and a nucleotide, which is the basic constituent unit of nucleic acids, includes naturally derived nucleotides as well as analogues thereof, in which sugar or base moieties are modified. The sequence of the nucleic acid encoding heavy- and light-chain variable regions of the present invention can vary. Such variation includes addition, deletion, or non-conservative or conservative substitution of nucleotides.

The DNA encoding the antibody can be easily separated or synthesized using conventional procedures (for example, using an oligonucleotide probe capable of specifically binding to DNA encoding heavy and light chains of the antibody) and can be inserted into an expression vector.

As used herein, the term "vector" refers to a means for expressing target genes in host cells, and includes plasmid vectors, cosmid vectors, and viral vectors such as bacteriophage vectors, adenovirus vectors, retroviral vectors and adeno-associated viral vectors. Vector components generally include, but are not limited to, one or more of the following components: signal sequences, replication origins, one or more antibiotic resistance marker genes, enhancer elements, promoters, and transcription termination sequences. The nucleic acid encoding the antibody is operably linked to promoters, transcription termination sequences or the like.

The term "operably linked" means functional linkage between a nucleic acid expression regulation sequence (e.g., array of the binding site of the promoter, signal sequence or transcription regulator) and another nucleic acid sequence, and enables the regulation sequence to regulate the transcription and/or translation of the other nucleic acid sequence.

When a prokaryotic cell is used as a host, it generally includes a potent promoter capable of conducting transcription (such as a tac promoter, lac promoter, lacUV5 promoter, lpp promoter, pLλ promoter, pRλ promoter, rac5 promoter, amp promoter, recA promoter, SP6 promoter, trp promoter, or T7 promoter), a ribosome-binding site for initiation of translation, and a transcription/translation termination sequence. In addition, for example, when a eukaryotic cell is used as a host, it includes a promoter derived from the genome of mammalian cells (e.g., a metallothionein promoter, a β-actin promoter, a human hemoglobin promoter or a human muscle creatine promoter), or a promoter derived from a mammalian virus (e.g., an adenovirus late promoter, vaccinia virus 7.5K promoter, SV40 promoter, cytomegalovirus (CMV) promoter, HSV tk promoter, mouse mammary tumor virus (MMTV) promoter, HIV LTR promoter, Moloney virus promoter, Epstein-Barr virus (EBV) promoter, or Rous sarcoma virus (RSV) promoter), and generally has a polyadenylation sequence as a transcription termination sequence.

Optionally, the vector may be fused with another sequence in order to facilitate purification of the antibody expressed thereby. The sequence to be fused includes, for example, glutathione S-transferase (Pharmacia, USA), maltose-binding protein (NEB, USA), FLAG (IBI, USA), 6×His (hexahistidine; Qiagen, USA) and the like.

The vector includes antibiotic-resistant genes commonly used in the art as selectable markers, and examples thereof include genes conferring resistance to ampicillin, gentamycin, carbenicillin, chloramphenicol, streptomycin, kanamycin, geneticin, neomycin and tetracycline.

In another aspect, the present invention is directed to a cell transformed with the above-mentioned vector. The cell used to produce the antibody of the present invention may be a prokaryote, yeast or higher eukaryotic cell, but is not limited thereto.

Prokaryotic host cells such as *Escherichia coli*, strains of the genus *Bacillus*, such as *Bacillus subtilis* and *Bacillus thuringiensis*, *Streptomyces* spp., *Pseudomonas* spp. (for example, *Pseudomonas putida*), *Proteus mirabilis* and *Staphylococcus* spp. (for example, *Staphylococcus carnosus*) may be used.

Interest in animal cells is the greatest, and examples of useful host cell lines include, but are not limited to, COS-7, BHK, CHO, CHOK1, DXB-11, DG-44, CHO/-DHFR, CV1, COS-7, HEK293, BHK, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U20S, and HT1080.

In another aspect, the present invention is directed to a method of producing the antibody or antigen-binding fragment thereof including: (a) culturing the cell; and (b) recovering an antibody or antigen-binding fragment thereof from the cultured cell.

The cells can be cultured in various media. Any commercially available medium can be used as a culture medium without limitation. All other essential supplements well-known to those skilled in the art may be included in appropriate concentrations. Culture conditions such as temperature and pH are conventionally used with host cells selected for expression, as will be apparent to those skilled in the art.

The recovery of the antibody or antigen-binding fragment thereof can be carried out, for example, by centrifugation or ultrafiltration to remove impurities and purification of the resulting product using, for example, affinity chromatography. Other additional purification techniques, such as anion or cation exchange chromatography, hydrophobic interaction chromatography, and hydroxyapatite (HA) chromatography, may be used.

In another aspect, the present invention is directed to a composition for preventing or treating a tumor including the antibody as an active ingredient. The antibody may be IgG or a fragment including a variable region, namely ScFv or Fab. In addition, the variable region of the heavy chain may be IgG1, IgG2, IgG3 or IgG4.

The present invention may provide, for example, a pharmaceutical composition for preventing or treating a tumor containing: (a) a pharmaceutically effective amount of the antibody to PD-L1 or antigen-binding fragment thereof according to the present invention; and (b) a pharmaceutically acceptable carrier. The present invention also relates to a method for preventing treating a tumor including administering the antibody or an antigen-binding fragment thereof according to the present invention to a patient with a tumor. The present invention may provide the use of the antibody or antigen-binding fragment thereof for the inhibition of the immunosuppressive mechanism of PD-L1 and the use thereof for the prevention or treatment of a tumor.

Tumors, which are the diseases to which the composition can be applied, include typical tumors or cancers that respond to immunotherapy, as well as tumors or cancers that have not been treated with immunotherapy to date. Non-limiting examples of tumors or cancers that are targets of treatment include melanoma (e.g., metastatic malignant melanoma), kidney cancer (e.g., clear cell carcinoma), prostate cancer (e.g., hormone refractory prostate adenocarcinoma), pancreatic adenocarcinoma, breast cancer, colon cancer, lung cancer (e.g., non-small cell lung cancer), esophageal cancer, head and neck squamous cell carcinoma, liver cancer, ovarian cancer, cervical cancer, thyroid cancer, glioblastoma, glioma, leukemia, lymphoma, and other neoplastic carcinomas. In addition, the tumors or cancers according to the present invention include refractory or recurrent cancers that can be treated using the antibody of the present invention.

In another aspect, the present invention is directed to a composition for preventing or treating a tumor including the antibody as an active ingredient. The antibody may be IgG or a fragment including a variable region, namely ScFv or Fab. In addition, the subtype of the heavy chain may be IgG1, IgG2, IgG3 or IgG4.

As used herein, the term "prevention" refers to any action causing the suppression of growth of a tumor or the delay of progression of a tumor by administration of the composition according to the present invention. The term "treatment" means suppression of the progression of a tumor, or alleviation or elimination of a tumor.

In some cases, it is possible to effectively target tumor cells using the antibody in combination with another anti-cancer therapeutic agent, and it is possible to enhance the immune response targeting tumor cells by increasing anti-tumor T cell activity. The antibody may be used in combination with: other anti-neoplastic or immunogenic agents [e.g., attenuated cancer cells, tumor antigens (including recombinant proteins, peptides and carbohydrate molecules), antigen transfer cells, for example, tumor-derived antigens or nucleic-acid-pulsed dendritic cells, immunostimulating cytokines (e.g., IL-2, IFNα2, and GM-CSF), and cells transfected with genes encoding immunostimulating cytokines (including for example but not limited to GM-CSF)]; standard cancer therapy (e.g. chemotherapy, radiotherapy or surgery); or other antibodies (including but not limited to VEGF, EGFR, Her2/neu, VEGF receptors, other growth factor receptors, CD20, CD40, CTLA-4, OX-40, 4-IBB, and ICOS).

In another aspect, the present invention is directed to a composition for co-administration with an antibody other than a PD-L1 antibody, the composition containing the antibody or an antigen-binding fragment thereof. Examples of the antibody other than the PD-L1 antibody include other antibodies mentioned above, for example, anti-VEGF, EGFR, Her2/neu, VEGF receptors, other growth factor receptors, CD20, CD40, CTLA-4, OX-40, 4-IBB, or an ICOS antibody. In another aspect, the present invention is directed to a method of preventing or treating a tumor, the method including administering the antibody or an antigen-binding fragment thereof in combination with an antibody other than a PD-L1 antibody to a patient with a tumor. In another aspect, the present invention is directed to the use of the antibody or antigen-binding fragment thereof for co-administration with an antibody other than a PD-L1 antibody to prevent or treat a tumor.

The antibody or antigen-binding fragment thereof may be administered simultaneously with the antibody other than a PD-L1 antibody, or may be administered separately therefrom with a time interval therebetween. The antibody other than a PD-L1 antibody may be separately administered before or after administration of the antibody or antigen-binding fragment thereof.

Since the composition uses the anti-PD-L1 antibody or an antigen-binding fragment thereof according to the present invention as an active ingredient, descriptions common thereto are omitted.

The pharmaceutically acceptable carrier contained in the composition according to the present invention may include a pharmaceutically acceptable carrier commonly used in preparations, and may include, but is not limited to, lactose, dextrose, sucrose, sorbitol, mannitol, starch, gum acacia, calcium phosphate, alginate, gelatin, calcium silicate, microcrystalline cellulose, polyvinylpyrrolidone, water, syrup, methylcellulose, methylhydroxybenzoate, propylhydroxybenzoate, talc, magnesium stearate, mineral oil, and the like. The composition according to the present invention may further contain a lubricant, a wetting agent, a sweetener, a flavoring agent, an emulsifier, a suspension agent, a preservative, or the like, in addition to the ingredients described above.

The pharmaceutical composition according to the present invention may be administered orally or parenterally. The parenteral administration may be intravenous injection, subcutaneous injection, intramuscular injection, intraperitoneal injection, endothelial administration, topical administration, intranasal administration, pulmonary administration, rectal administration or the like.

Upon oral administration, since proteins or peptides are digested, an oral composition should be coated with an active drug or formulated so as to protect the same from degradation in the stomach. In addition, the pharmaceutical composition may be administered using any device capable of delivering the active substance to target cells.

The suitable dose of the pharmaceutical composition according to the present invention may vary depending on factors such as the formulation method, administration method, and age, body weight, gender, pathological conditions, diet, administration time, administration route, excretion rate and responsiveness of the patient, and a general physician of ordinary skill can easily determine and prescribe a dose effective for the desired treatment or prevention. For example, the daily dose of the pharmaceutical composition according to the present invention may be within the range of 0.001 to 100 mg/kg. The term "pharmaceutically effective amount" may mean an amount sufficient to prevent or treat a cancer or an autoimmune disease.

The pharmaceutical composition according to the present invention may be prepared into a unit dose form, or may be incorporated into a multi-dose container through formulation using a pharmaceutically acceptable carrier and/or excipient according to a method that can be easily implemented by those skilled in the art to which the present invention pertains. Here, the formulation may be in the form of a solution, a suspension or an emulsion in an oil or aqueous medium, or may be in the form of an extract, a powder, a suppository, a granule, a tablet or a capsule. The composition may further contain a dispersant or a stabilizer.

EXAMPLE

Hereinafter, the present invention will be described in more detail with reference to examples. However, it will be obvious to those skilled in the art that these examples are provided only for illustration of the present invention and should not be construed as limiting the scope of the present invention.

Example 1. Biopanning of Antibodies Binding to PD-L1

Human naive ScFv (scFv) libraries disclosed in Korean Patent Laid-Open No. 10-2008-0109417 were used to antibody libraries for screening antibodies binding to PD-L1 and preparation of the libraries. A general biopanning method was used, and human and mouse PD-L1 proteins were optionally used to screen antibodies having cross-reactivity between human and mouse.

Human or mouse PD-L1-HisTag (#10084-H08H/50010-M08H, Sino Biological Inc. CN) was prepared at a concentration of 2 g/ml, and 100 µl of the prepared PD-L1-HisTag was added to each well of a 96-well nickel-coated late (#15142, Thermo Fisher Scientific) and allowed to stand at 4° C. overnight to induce adsorption. The following day, after washing three times with PBS, 200 µl of a 2% BSA-containing PBS solution was added thereto and allowed to stand at room temperature for 2 hours. After washing three times with PBS, 100 µl of a 2% BSA-containing phage library solution was added to each well, rocked at room temperature for 30 minutes, and allowed to stand for 2 hours to induce binding of the library and antigen. After removing the supernatant, the cells were washed 5 times with PBS containing 0.05% Tween-20 (hereinafter, referred to as "PBST") and washed 5 times with PBS, and 100 µl of a 100 mM trimethylamine solution was added thereto to elute the PD-L1-bound phage. After the reaction was allowed to proceed for 10 minutes, 50 µl of 1M Tris-HCl (pH 7.5) was added to perform neutralization, and the supernatant was added to 10 ml of a growing XL-1 Blue E. coli strain culture solution ($OD_{600}$=0.5) and mixed therewith to induce transfection at 37° C. for 30 minutes. After centrifugation, the cells were resuspended in a small amount of medium and spread on a 2×YT-Agar plate containing 1% glucose and 34 mg/ml chloramphenicol. After culturing at 30° C. for 16 hours, all colonies on the plate were collected to obtain PD-L1-binding phage-infected XL-1 Blue. The phage was amplified through culture of the XL-1 Blue E. coli and induction of phage production, and was then isolated using a PEG-precipitation method. The resulting phage solution was used as a library for the subsequent biopanning, and phage clones having a desired binding pattern were obtained through selective use of human and mouse PD-1, and regulation of binding stringency.

XL-1 Blue transinfected with PD-L1-binding phage in the final stage of biopanning was spread on a 2×YT-agar plate containing 34 q/ml chloramphenicol and cultured at 37° C. for 16 hours. The formed single colonies were randomly selected and then shake-cultured overnight at 37° C. on a 96-deep well plate (Bioner, KR) containing 200 µl of a culture medium (2×YT medium containing 34 g/ml chloramphenicol) so that each clone could be distinguished from one another. Then, the resulting product was used as a PD-L1-binding phage mono-clone, glycerol was added thereto to obtain a final concentration of 20%, and then the result was cryopreserved.

Example 2: Screening of scFv Phage Specifically Binding to PD-L1 (ELISA/FACS)

A portion of the preserved PD-L1-binding phage monoclonal solution was added to 200 µl of a fresh culture medium, was shake-cultured at 37° C. for 1 to 2 hours until the logarithmic growth phase was reached, and was then transfected with a M13 helper phage at 37° C. for 30 minutes. Subsequently, the medium was exchanged with a culture medium containing 70 µg/ml kanamycin, 1 mM IPTG, and 5 mM $MgCl_2$ and was then shake-cultured at 30° C. overnight. After centrifugation, the supernatant was used as a culture solution containing a PD-L1-binding monoclonal phage for the binding test and screening.

100 µl of a solution in 1 µg/ml of a His-tag human or mouse PD-L1 protein (Sino Biological Inc. CN) was added to each well of a 96-well immunoplate (Nunc, US) and then allowed to stand at 4° C. overnight to induce adsorption. The following day, washing was performed three times with PBS containing 0.05% Tween-20 (hereinafter, referred to as "PBST"), 200 µl of a 2% BSA/PBST solution was added to each well, and the resulting solution was allowed to stand at room temperature for 2 hours to induce blocking. After washing three times with PBST, 50 µl of 4% BSA-containing PBS and 50 µl of a monoclonal phage-containing culture solution were added to each well, and binding was allowed to proceed for 1 hour at room temperature. After washing three times with PBST, 100 µl of a solution of HRP-conjugated mouse anti-M13 monoclonal antibody (#27-9421-01, GE Healthcare, US), diluted at a ratio of 1/3000 was added to PBST containing 2% BSA and was allowed to reacted at room temperature for 1 hour. After washing three times with PBST, color was developed using 100 µl of a TMB substrate reagent (#555214, BD Biosciences, US). The color development reaction was stopped by adding 50 µl of 2N $H_2SO_4$, and the specific absorbance, $OD_{450-630}$, was measured using a Sunrise microplate reader (TECAN, CH) (Table 1).

TABLE 1

| Clone | $OD_{450-630}$ | | Clone | $OD_{450-630}$ | |
|---|---|---|---|---|---|
| | hPD-L1 | mPD-L1 | | hPD-L1 | mPD-L1 |
| 1F9 | 1.09 | 1.17 | 2A8 | 1.38 | 0.07 |
| 2C9 | 1.35 | 1.09 | 1A10 | 1.09 | 0.05 |
| 3A12 | 1.10 | 0.45 | MB6 | 1.305 | 0.813 |
| 4E8 | 1.28 | 0.21 | ME10 | 1.319 | 1.129 |
| 4D9 | 1.31 | 0.76 | MB12 | 1.268 | 0.884 |
| 1G1 | 1.38 | 0.35 | ME4 | 1.655 | 1.438 |

Overexpressing cell lines (hPD-L1/CHO-K1, mPD-L1/CHO-K1), established by introducing human and mouse PD-L1 genes into CHO-K1 cells, were used for flow cytometry. Each cell was maintained and cultured, washed with PBS, suspended in 5 mM EDTA and then recovered through centrifugation. A cell suspension ($4 \times 10^6$ cells/ml) was prepared using a FACS-exclusive buffer (containing 2% FBS and PBS 0.05% sodium azide) and seeded at 50 µl/well into a 96-deep well plate. 50 µl of a monoclonal phage-containing culture solution was added and reacted at room temperature for 1 hour. After washing with 400 µl of FACS-exclusive buffer, 100 µl of a mouse anti-M13 monoclonal antibody solution diluted at a ratio of 1/500 was added and allowed to stand at 4° C. for 1 hour. After washing with 400 µl of FACS-exclusive buffer, 100 µl of a PE-conjugated anti-mouse IgG polyclonal antibody solution diluted at a ratio of 1/500 was added thereto and the result was allowed to stand at 1° C. for 1 hour to complete fluorescent labeling. After washing, 200 µl of FACS-exclusive buffer was added to suspend the cells, and each cell was analyzed using a flow cytometer FACSCalibur (BD Biosciences, US). As a positive control group, fluorescence labeling was conducted using FITC-conjugated anti-human PD-L1 antibody (#558065, BD Biosciences) and PE-conjugated anti-mouse PD-L1 (#558091, BD Biosciences). The analysis was performed using a FACSCalibur of BD Bioscience, and the results are shown in FIG. 1.

Example 3: Anti-PD-L1 IgG Expression

Conversion of the selected scFv phage to the IgG form was performed using molecular biology techniques. Phagemid was extracted from the selected E. Coli clone and double-cut with restriction enzyme Sfi I (R0123, New England Biolabs, US) to obtain a heavy-chain variable-region DNA fragment and pIgGHD-6A6Hvy, a vector containing a heavy-chain constant region was treated with Sfi I, and then a variable-region DNA fragment was inserted. In the same manner as above, the phagemid was double-cut with the restriction enzyme, BstX I (R0113, New England Biolabs), to obtain a light-chain variable-region DNA fragment, and pIgGLD-6A6Lgt, the vector containing a light-chain constant region was double-cut with BstX I, and then a variable-region DNA fragment was inserted to complete DNA cloning in the form of IgG.

For transient expression of IgG, an Expi293F expression system kit (Thermo Fisher Scientific, US) was used. Expi293 cells included in the kit were suspension-cultured in a 125 rpm orbital shaker at 37° C. and 5% $CO_2$ using a dedicated medium. Every 3 days, the cells were subcultured to a density of $3 \times 10^5$ cells/ml, and when the expression vector was introduced, the number of cells was adjusted to $3 \times 10^6$ cells/ml before use. Gene introduction was conducted using a dedicated reagent, ExpiFectamine, and a lipid-DNA complex containing 2.7 µl of ExpiFectamine and 1 µg of expression vector DNA and per 1 ml of cell suspension was prepared and added to the cell suspension. 16 to 18 hours after introduction, ½ of an enhancer was added to induce expression. Culture was conducted for 3 to 4 days under the same conditions, and the supernatant containing IgG was collected via centrifugation.

Example 4: Screening of Anti-PD-L1 Antibody Through Analysis of PD-1/PD-L1 Signal Inhibition Effect In order to evaluate the function of the obtained antibody, the degree of inhibition of the PD-1/PD-L1 signaling system was evaluated. For primary screening, IgG was temporarily expressed on a 2 ml scale using the method according to Example 3, and then the culture supernatant was collected and used for efficacy analysis.

The present test was performed using a commercially available PD-1/PD-L1 blockade bioassay (J1250, Promega Corp. US). For analysis, 0.5 ml of PD-L1-expressing CHO-K1 cells included in the kit were thawed in a growth medium (Ham's F-12 medium containing 10% FBS), seeded in an amount of 100 l in a 96-well microplate, and cultured at 37° C. in a 5% $CO_2$ environment overnight. The following day, 40 μl of an IgG transient expression culture supernatant and 40 μl of a PD-1 expression effector cell suspension (RPI1640 containing 1% FBS) adjusted to a concentration of 20 g/ml were added to each well and cultured for 6 hours. Then, 80 μl of a Bio-Glo reagent was added and reacted for 20 minutes. Then, luminescence was measured using a Hidex Chameleon instrument (FIG. 2). The measured luminescence was expressed as a relative value normalized based on 100% of an atezolizumab-treated group used as a positive control group. As a result of the measurement, it was determined that PD-1/PD-L1 signal inhibition is possible in clones 1G1 and ME4, determined to be positive for luminescence. The CDR sequences of each of 1G1 and ME4 are shown in Table 2 below.

TABLE 2

(Please note AA sequence of SEQ ID No. 1 has been amended, according to sequences of Table 5)

|  |  | Amino acid sequence | SEQ ID No. |
|---|---|---|---|
| IG1 | VH_CDR1 | GTGFDDYA | 1 |
|  | VH_CDR2 | ISWNSGSI | 2 |
|  | VH_CDR3 | AKPRDISSWLGMDV | 3 |
|  | VL_CDR1 | QSISSW | 4 |
|  | VL_CDR2 | AAS | 5 |
|  | VL_CDR3 | QQTNNFPYT | 6 |
| ME4 | VH_CDR1 | GGTFNNYA | 7 |
|  | VH_CDR2 | IIPILGIA | 8 |
|  | VH_CDR3 | ARSYSGYAEGAFDI | 9 |
|  | VL_CDR1 | SSNIGAGYD | 10 |
|  | VL_CDR2 | GNS | 11 |
|  | VL_CDR3 | QSYDSRLSGPV | 12 |

Example 5: Purification of Anti-PD-L1 Antibody

The obtained supernatant was injected into a Protein A column (GE Healthcare) and then IgG was purified through affinity chromatography. The column was equilibrated with 20 mM Tris-HCl, 50 mM NaCl, and 5 mM EDTA (pH 7.0), the supernatant was added, and the result was washed with a solution of 50 mM Tris-HCl, 500 mM NaCl, 5 mM EDTA, and 0.2% polysorbate 20 (pH 7.0), was eluted with 50 mM NaCl and 0.1 M glycine-HCl (pH 3.5), and was neutralized with 1 M Tris. The solvent was replaced with PBS through dialysis using a MWCO 10,000 spectra/por dialysis membrane (Spectrum Labs, US) for eluted proteins. Then, the result was concentrated to a desired concentration using a Vivaspin (Sartorius, DE) and then seeded and stored at −80° C.

After purification, each antibody was treated with a non-reducing and reducing LDS sample buffer (Thermo Fisher Scientific) and electrophoresed using a NuPAGE System (Thermo Fisher Scientific). As a result, IgG having a total molecular weight of about 150 kDa, including a 50 kDa heavy chain and a 25 kDa light chain, was obtained (FIG. 3).

Example 6: Analysis of Binding Specificity of Anti-PD-L1 Antibody

ELISA and flow cytometry were used for binding specificity analysis, and binding constants were measured using an Octet system (Pall ForteBio LLC. US).

100 μl of a solution in 1 μg/ml of a His-tag human or mouse PD-L1 protein (Sino Biological Inc. CN) was added to each well of a 96-well immunoplate (Nunc, US) and then allowed to stand at 4° C. overnight to induce adsorption. The following day, washing was performed three times with PBS containing 0.05% Tween-20 (hereinafter, referred to as "PBST"), 200 μl, of a 2% BSA/PBST solution was added to each well, and the resulting solution was allowed to stand at room temperature for 2 hours to induce blocking. After washing three times with PBST, 1 μg/ml of each test antibody solution was added in an amount of 100 μl for 1 hour at room temperature and washed 3 times with PBST, and 100 μl of an HRP-conjugated anti-His tag monoclonal antibody (MAB050H, R & D systems, US), diluted at 1:2000, was added and reacted at room temperature for 1 hour to induce binding. After washing three times with PBST, color was developed using 100 μl of a TMB substrate reagent. The color development reaction was stopped by adding 50 μl of 2N $H_2SO_4$, and the specific absorbance, $OD_{450-630}$, was measured using a Sunrise microplate reader (TECAN, CH) (FIG. 4).

For flow cytometry, overexpressing cell lines (hPD-L1/CHO-K1, mPD-L1/CHO-K1), established by introducing human and mouse PD-L1 genes into CHO-K1 cells, were used. Each cell was maintained and cultured, washed with PBS, suspended in 5 mM EDTA and then recovered through centrifugation. A cell suspension ($5\times10^6$ cells/ml) was prepared using a FACS-exclusive buffer (containing 2% FBS and PBS 0.05% sodium azide), and was seeded at 100 μl/tube. 2 g/ml of a test antibody was added at 100 μl to each test tube and then allowed to stand at 4° C. for 30 minutes to induce antibody-cell binding. Then, the cells were washed using 2 ml of FACS buffer, 100 μl of a secondary antibody dilution (1/500, PE-conjugated anti-human IgG-Fc polyclonal antibody fragment, #A80-248PE, Bethyl Laboratories Inc. US) was added thereto, and then the mixture was allowed to stand at 4° C. for 20 minutes to induce fluorescent labeling. After washing with 2 ml of FACS buffer, 200 μl of FACS buffer was added to suspend the cells. As a positive control group, fluorescence labeling was conducted using FITC-conjugated anti-human PD-L1 antibody (#558065, BD Biosciences) and PE-conjugated anti-mouse PD-1 (#558091, BD Biosciences). The analysis was performed using a FACSCalibur of BD Bioscience and the results are shown in FIG. 5.

The binding ability of the selected anti-PD-L1 antibody to human or mouse PD-L1 was measured using the Octet system (Fortebio Inc. US). For this purpose, an anti-PD-L1 antibody was fixed on a biosensor, and binding kinetics at each concentration of human or mouse PD-L1 were measured to calculate a binding rate constant ($k_a$), a dissociation rate constant ($k_{dis}$) and a binding constant ($K_D$) (Table 3).

TABLE 3

| Sample | human PD-L1 | | | mouse PD-L1 | | |
|---|---|---|---|---|---|---|
| | $K_D(M)$ | $k_{on}(1/Ms)$ | $k_{dis}(1/s)$ | $K_D(M)$ | $k_{on}(1/Ms)$ | $k_{dis}(1/s)$ |
| ME4 | $1.72 \times 10^{-9}$ | $1.88 \times 10^3$ | $3.24 \times 10^{-4}$ | $3.74 \times 10^{-8}$ | $5.63 \times 10^4$ | $2.11 \times 10^{-3}$ |
| IG1 | $6.29 \times 10^{-10}$ | $2.32 \times 10^3$ | $1.46 \times 10^{-4}$ | — | — | — |
| Atezolizumab | $3.02 \times 10^{-10}$ | $2.78 \times 10^3$ | $8.38 \times 10^{-5}$ | $3.58 \times 10^{-10}$ | $3.43 \times 10^5$ | $1.23 \times 10^{-4}$ |

Example 7: Analysis of PD-1/PD-L1 Signal Inhibition Effect of Anti-PD-L1 Antibody In order to evaluate the function of the obtained antibody, the degree of inhibition of the PD-1/PD-L1 signaling system was evaluated. The present test was performed using a commercially available PD-1/PD-L1 blockade bioassay (J1250, Promega Corp. US) in the same manner as in Example 4 above. For analysis, 0.5 ml of PD-L1-expressing CHO-K1 cells included in the kit were thawed in a growth medium (Ham's F-12 medium containing 10% FBS), seeded in an amount of 100 μl in a 96-well microplate, and cultured at 37° C. in a 5% $CO_2$ environment overnight. The following day, the culture solution was removed and 40 μl of 10 μg/ml of each antibody solution (isotype control, atezolizumab, $1G^1$, ME4) and 40 μl of a cell suspension prepared by suspending PD-1-expressing effector cells in an assay medium (RPM1640 with 1% FBS) were added to each well, culture was performed for 6 hours, and a reaction with 80 Gl of Bio-Glo reagent was allowed to occur for 20 minutes. Then, luminescence was measured using a Hidex Chameleon instrument (FIG. 6). As a result, it was determined that the IgG-type antibodies 1G1 and ME4 retained PD-1/PD-L1 inhibitory activity even after purification.

Example 8: In Vivo Anti-Tumor Effect Analysis

In order to analyze the anti-tumor effect of the anti-PD-L1 antibody, an allograft model of a mouse-derived colon cancer cell line (MC-38) was used. A MC-38 mouse colon cancer cell line was maintained and cultured at 37° C. and 5% $CO_2$. 5-week-old SPF female C57BL/6 mice (Koatech, KR) were obtained and acclimated for 1 week, and $5 \times 10^6$ cells/ml of a MC38 cell suspension was transplanted at a concentration of 200 μl/mouse subcutaneously between the axillary area between the right shoulder blade and the chest wall. Following cancer cell transplantation, when a tumor was formed at a size of 41.4 $mm^3$, each of a vehicle control and anti-PD-L1 antibodies ME4 and atezolizumab was administered at 10 mg/kg thereto twice a week, and body weight and tumor size were measured. The tumor size was measured in three directions using a Vernier caliper, and then calculated using the calculation formula of length×width×height/2.

The group administered with the anti-PD-L1 antibody exhibited statistically significant tumorigenic inhibitory effects on day 2, day 5, and day 7, specifically 10.4%, 22.4% and 24.2%, respectively, compared to the vehicle control group. The control drug, atezolizumab, showed tumor growth inhibitory effects of 29.2%, 35.8%, 29.6% and 31.1% on days 2, 5, 7 and 9, respectively (FIG. 7). Although both the group treated with ME4 and the group treated with atezolizumab showed a decrease in tumor growth inhibitory effect after day 9, this was determined to be due to immunogenicity due to administration of human antibodies.

Example 9: Construction and Selection of Mutants to Enhance Affinity

Antibody optimization was performed to enhance the affinity of the anti-PD-L1 antibody clones 1G1 and ME4. Primers obtained by introducing random mutations into light-chain CDR3 of 1G1 and heavy-chain CDR3 of ME4 were produced using a soft-randomization method for preserving 70% of the original DNA sequences of each of 1G1 and ME4 and randomizing the same. DNA fragments encoding a light-chain variable region of 1G1 and a heavy-chain variable region of ME4, into which a mutation was introduced, were obtained through PCR using the primers. The DNA fragments encoding a light-chain variable region of 1G1 and a heavy-chain variable region of ME4 were substituted with a light-chain variable region of a 1G1 scFv phage phagemid and a heavy-chain variable region of a ME4 scFv phage phagemid, respectively, to prepare a 1G1 light-chain CDR3 mutant scFv phage library and a ME4 heavy-chain CDR3 mutant scFv phage DNA library, respectively.

The mutant scFv phage DNA library was purified using phenol-chloroform and was transformed into the E. coli strain XL-1 Blue using electroporation. Diversity acquisition was confirmed through transformation efficiency analysis and DNA sequence analysis, phage expression was induced by culturing in a 500 ml scale, and a 1G1 light-chain CDR3 mutant scFv phage library and a ME4 heavy-chain CDR3 mutant scFv phage library were cultured using a PEG-precipitation method.

Biopanning was performed in the same manner as in Example 1 using each mutant scFv phage library. Then, in the selection process, the dissociation rate constant $k_{dis}$ of scFv was measured as a quantitative evaluation index of the ability to maintain binding. The resultant amino acid sequences (Tables 4 and 5) and the dissociation rate constant measurements (Table 6) associated with the selected optimized clones are shown.

TABLE 4

| | | Amino acid sequece | SEQ ID NO. |
|---|---|---|---|
| IG1.D8 | VL_CDR3 | QQTTNFPYT | 13 |
| IG1.E12 | VL_CDR3 | QQYVTFPYT | 14 |
| ME4.A2 | VH_CDR3 | ARSSRGYAHGAFDI | 15 |
| ME4.A11 | VH_CDR3 | ARSRGGYAHGAFDI | 16 |
| ME4.A12 | VH_CDR3 | ARSHWGYAHGAFDI | 17 |
| ME4.B10 | VH_CDR3 | ARSARGYAHGAFDI | 18 |
| ME4.B12 | VH_CDR3 | ARSSFGYSVGAFDI | 19 |

TABLE 5

| Sequence name | | Amino acid sequence | SEQ ID NO. |
|---|---|---|---|
| 1G1 | VH | QVQLVESGGGLVQPGRSLRLSCAAS GFTFDDYAMHWVRQAPGKGLEWVSGISWNSGSI GYADSVKGRFTISRDNAKNSLYLQMNSLRAEDTAV YYCAKPRDISSWLGMDVWGQGTTVTVSS | 20 |
| | VL | DIQMTQSPSSVSASVGDRVTITCRAS QDISSWLAWYQQKPGKAPKLLIYAASSLQ SGVPSRFSGSGSGTDFTLTISSLQPEDSAT YYCQQTNNFPYTFGQGTKLEIKR | 21 |
| 1G1.D8 | VL | DIQMTQSPSSVSASVGDRVTITCRAS QSISSWLAWYQQKPGKAPKLLIYAASSLQ SGVPSRFSGSGSGTDFTLTISSLQPEDSAT YYCQQTTNFPYTFGQGTKLEIKR | 22 |
| 1G1.E12 | VL | DIQMTQSPSSVSASVGDRVTITCRAS QSISSWLAWYQQKPGKAPKLLIYAASSLQ SGVPSRFSGSGSGTDFTLTISSLQPEDSAT YYCQQTVTFPYTFGQGTKLEIKR | 23 |
| ME4 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSYSGYAEGAFDIWGQGTMVTVSS | 24 |
| | VL | QFVLTQPPSVSGAPGQRVTISCTGS SSNIGAGYDVHWYQQLPGTAPKVLIYGNSDRP SGVPDRFSGSKSGTSASLAITGLQGEDKAT YYCQSYDSRLSGPVFGEGTKVTVLG | 25 |
| ME4.A2 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSSRGYAHGAFDIWGQGTMVTVSS | 26 |
| ME4.A11 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSRGGYAHGAFDIWGQGTMVTVSS | 27 |
| ME4.A12 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSHWGYAHGAFDIWGQGTMVTVSS | 28 |
| ME4.B10 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSARGYAHGAFDIWGQGTMVTVSS | 29 |
| ME4.B12 | VH | QVQLVESGAEVKKPGSSVKVSCKAS GGTFNNYAVSWVRQAPGQGLEWMGRIIPILGIA NYAQTFQGRVTITADKSTTTAYMELSSLRSEDTAV YYCARSSFGYSVGAFDIWGQGTMVTVSS | 30 |

TABLE 6

| | $k_{dis}$ (1/s) | |
|---|---|---|
| Phage Clone | hPD-L1 | mPD-L1 |
| 1G1 | $1.52 \times 10^{-4}$ | — |
| 1G1.D8 | $2.42 \times 10^{-4}$ | — |
| 1G1.E12 | $2.68 \times 10^{-4}$ | — |
| ME4 | $1.86 \times 10^{-4}$ | $3.74 \times 10^{-4}$ |
| ME4.A2 | $1.83 \times 10^{-4}$ | $8.52 \times 10^{-4}$ |
| ME4.A11 | $7.86 \times 10^{-5}$ | $4.86 \times 10^{-4}$ |
| ME4.A12 | $<1.0 \times 10^{-7}$ | $1.01 \times 10^{-3}$ |
| ME4.B10 | $1.60 \times 10^{-4}$ | $4.67 \times 10^{-4}$ |
| ME4.B12 | $1.77 \times 10^{-4}$ | $7.53 \times 10^{-4}$ |

Example 10: Analysis of PD-1/PD-L1 Signal Inhibition Effect of Optimized Anti-PD-L1 Antibody Each optimized scFv phage clone was converted to IgG form. DNA cloning, production and purification methods for specific morphology conversion were performed in the same manner as in Examples 3 and 5. In order to evaluate the function of the obtained antibody, the degree of inhibition of the PD-1/PD-L1 signaling system was evaluated. The culture supernatant of the optimized IgG, transiently expressed on a 2 ml scale, was collected and used for efficacy analysis. PD-1/PD-L1 signal inhibition was evaluated in the same manner as in Example 4 (FIG. 8). As a result, five clones derived from ME4 exhibited improved PD-1/PD-L1 signal inhibition efficacy compared to the parent antibody, whereas two clones derived from 1G1 inhibited PD-1/PD-L1 signals, but efficacy was not significantly different from that of 1G1.

In particular, after production and purification of B10 and B12 IgG, the concentration dependency of PD-1/PD-L1 signal inhibition effect was analyzed (FIG. 9). The result proved that both antibodies were able to inhibit PD-1/PD-L1 signals in a concentration-dependent manner, and showed that they exhibited higher maximum activity than atezolizumab.

Example 11: Analysis of Physicochemical Properties of Optimized Anti-PD-L1 Antibody The cell-binding ability of the optimized anti-PD-L1 antibody was measured through flow cytometry. The experiment was performed in the same manner as in Example 6. As can be seen from FIG. 10, ME4.A2, ME4.A11, ME4.A12, ME4.B10 and ME4.B12 bound to both human and mouse PD-L1. In order to evaluate binding force, binding kinetics were analyzed using Octet and the binding constant was calculated (Table 7). Through optimization, it was confirmed that the binding ability to human and mouse PD-L1 was significantly increased. In particular, it is determined that an increase in binding ability to mouse PD-L1 is more advantageous for the efficacy test in animal models.

TABLE 7

| Sample | human PD-L1 | | | mouse PD-L1 | | |
|---|---|---|---|---|---|---|
| | $K_D(M)$ | $k_{on}(1/Ms)$ | $k_{dis}(1/s)$ | $K_D(M)$ | $k_{on}(1/Ms)$ | $k_{dis}(1/s)$ |
| ME4 | $1.72 \times 10^{-9}$ | $1.88 \times 10^5$ | $3.24 \times 10^{-4}$ | $3.74 \times 10^{-8}$ | $5.63 \times 10^4$ | $2.11 \times 10^{-3}$ |
| ME4.A2 | $5.86 \times 10^{-11}$ | $1.74 \times 10^5$ | $1.02 \times 10^{-5}$ | $3.01 \times 10^{-9}$ | $3.28 \times 10^5$ | $9.86 \times 10^{-4}$ |
| ME4.A11 | $9.18 \times 10^{-10}$ | $1.18 \times 10^5$ | $1.09 \times 10^{-4}$ | $4.86 \times 10^{-9}$ | $1.29 \times 10^5$ | $6.26 \times 10^{-4}$ |
| ME4.A12 | $1.34 \times 10^{-10}$ | $1.65 \times 10^5$ | $2.20 \times 10^{-5}$ | $2.65 \times 10^{-9}$ | $3.08 \times 10^5$ | $8.17 \times 10^{-4}$ |
| ME4.B10 | $1.67 \times 10^{-10}$ | $1.45 \times 10^5$ | $1.45 \times 10^{-5}$ | $1.62 \times 10^{-9}$ | $2.60 \times 10^5$ | $4.22 \times 10^{-4}$ |
| ME4.B12 | $1.94 \times 10^{-11}$ | $1.64 \times 10^5$ | $3.19 \times 10^{-6}$ | $1.22 \times 10^{-9}$ | $3.10 \times 10^5$ | $3.79 \times 10^{-4}$ |
| Atezolizumab | $3.02 \times 10^{-10}$ | $2.78 \times 10^5$ | $8.38 \times 10^{-5}$ | $3.58 \times 10^{-10}$ | $3.43 \times 10^5$ | $1.23 \times 10^{-4}$ |

INDUSTRIAL APPLICABILITY

The anti-PD-L1 antibody or antigen-binding fragment thereof according to the present invention exhibits desired binding ability to PD-L1 and can be useful for the prevention or treatment of a target tumor. The present invention is capable of providing a single therapy and a combination therapy with other conventional therapeutic agents, thereby developing a therapeutic agent having higher efficacy than a conventional anti-PD-L1 antibody.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

What is claimed is:

1. An antibody binding to PD-L1 or an antigen-binding fragment thereof, comprising:
   a heavy-chain variable region comprising a heavy-chain CDR1 of SEQ ID NO: 1, a heavy-chain CDR2 of SEQ ID NO: 2, and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 6;
   a heavy-chain variable region comprising a heavy-chain CDR1 of SEQ ID NO: 1, a heavy-chain CDR2 of SEQ ID NO: 2, and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 13;
   a heavy-chain variable region comprising a heavy-chain CDR1 of SEQ ID NO: 1, a heavy-chain CDR2 of SEQ ID NO: 2, and a heavy-chain CDR3 of SEQ ID NO: 3, and a light-chain variable region comprising a light-chain CDR1 of SEQ ID NO: 4, a light-chain CDR2 of SEQ ID NO: 5, and a light-chain CDR3 of SEQ ID NO: 14;
   a heavy-chain variable region comprising a heavy-chain CDR1 of SEQ ID NO: 7, a heavy-chain CDR2 of SEQ ID NO: 8, and a heavy-chain CDR3 of SEQ ID NO: 9, and a light-chain variable region comprising a light-chain CDR1 of SEQ ID NO: 10, a light-chain CDR2 of SEQ ID NO: 11, and a light-chain CDR3 of SEQ ID NO: 12;
   a heavy-chain variable region comprising a heavy-chain CDR1 of SEQ ID NO: 7, a heavy-chain CDR2 of SEQ ID NO: 8, and a heavy-chain CDR3 of SEQ ID NO: 15, and a light-chain variable region comprising a light-chain CDR1 of SEQ ID NO: 10, a light-chain CDR2 of SEQ ID NO: 11, and a light-chain CDR3 of SEQ ID NO: 12;
   a heavy-chain variable region comprising a heavy-chain CDR1 of SEQ ID NO: 7, a heavy-chain CDR2 of SEQ ID NO: 8, and a heavy-chain CDR3 of SEQ ID NO: 16, and a light-chain variable region comprising a light-chain CDR1 of SEQ ID NO: 10, a light-chain CDR2 of SEQ ID NO: 11, and a light-chain CDR3 of SEQ ID NO: 12;
   a heavy-chain variable region comprising a heavy-chain CDR1 of SEQ ID NO: 7, a heavy-chain CDR2 of SEQ ID NO: 8, and a heavy-chain CDR3 of SEQ ID NO: 17, and a light-chain variable region comprising a light-chain CDR1 of SEQ ID NO: 10, a light-chain CDR2 of SEQ ID NO: 11, and a light-chain CDR3 of SEQ ID NO: 12;
   a heavy-chain variable region comprising a heavy-chain CDR1 of SEQ ID NO: 7, a heavy-chain CDR2 of SEQ ID NO: 8, and a heavy-chain CDR3 of SEQ ID NO: 18, and a light-chain variable region comprising a light-chain CDR1 of SEQ ID NO: 10, a light-chain CDR2 of SEQ ID NO: 11, and a light-chain CDR3 of SEQ ID NO: 12; and
   a heavy-chain variable region comprising a heavy-chain CDR1 of SEQ ID NO: 7, a heavy-chain CDR2 of SEQ ID NO: 8, and a heavy-chain CDR3 of SEQ ID NO: 19, and a light-chain variable region comprising a light-chain CDR1 of SEQ ID NO: 10, a light-chain CDR2 of SEQ ID NO: 11, and a light-chain CDR3 of SEQ ID NO: 12.

2. The anti-PD-L1 antibody or an antigen-binding fragment thereof according to claim 1, comprising:
   a heavy-chain variable region selected from the group consisting of SEQ ID NOS: 20, 24, 26, 27, 28, 29 and 30.

3. The anti-PD-L1 antibody or an antigen-binding fragment thereof according to claim 1, comprising:
   a light-chain variable region selected from the group consisting of SEQ ID NOS: 21, 22, 23 and 25.

4. A nucleic acid encoding the antibody or an antigen-binding fragment thereof according to claim 1.

5. An expression vector comprising the nucleic acid according to claim 4.

6. A cell transformed with the expression vector according to claim 5.

7. A method for producing an antibody binding to PD-L1 or an antigen-binding fragment thereof, comprising:
   (a) culturing the cell according to claim 6; and
   (b) recovering the antibody or antigen-binding fragment thereof from the cultured cell.

8. A composition for preventing or treating a tumor comprising the antibody or antigen-binding fragment thereof according to claim 1 as an active ingredient.

9. A composition for co-administration with an antibody other than an antibody binding to PD-L1, the composition comprising the antibody or antigen-binding fragment thereof according to claim 1.

\* \* \* \* \*